(12) United States Patent
Wang et al.

(10) Patent No.: US 10,386,301 B2
(45) Date of Patent: Aug. 20, 2019

(54) TOP-DOWN AND ROTATIONAL SIDE VIEW BIOPSY SPECIMEN IMAGER AND METHODS

(71) Applicant: LI-COR, Inc., Lincoln, NE (US)

(72) Inventors: Han-Wei Wang, Lincoln, NE (US); Lyle R. Middendorf, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 0 days.

(21) Appl. No.: 15/955,567

(22) Filed: Apr. 17, 2018

(65) Prior Publication Data

US 2018/0306720 A1 Oct. 25, 2018

Related U.S. Application Data

(60) Provisional application No. 62/489,921, filed on Apr. 25, 2017.

(51) Int. Cl.
*G01N 21/64* (2006.01)
*G06T 1/00* (2006.01)
*G01N 21/17* (2006.01)

(52) U.S. Cl.
CPC ..... *G01N 21/6458* (2013.01); *G01N 21/6428* (2013.01); *G06T 1/0007* (2013.01); *G01N 2021/177* (2013.01); *G01N 2021/1787* (2013.01); *G01N 2021/6439* (2013.01)

(58) Field of Classification Search
CPC .................................................. G01N 21/6458
See application file for complete search history.

(56) References Cited

U.S. PATENT DOCUMENTS

| | | | |
|---|---|---|---|
| 2,792,502 | A | 5/1957 | O'Connor et al. |
| 5,103,338 | A | 4/1992 | Crowley et al. |
| 5,224,141 | A | 6/1993 | Yassa et al. |
| 5,408,294 | A | 4/1995 | Lam |

(Continued)

FOREIGN PATENT DOCUMENTS

| | | |
|---|---|---|
| CN | 101301192 | 11/2008 |
| CN | 102048525 | 5/2012 |

(Continued)

OTHER PUBLICATIONS

U.S. Appl. No. 15/352,427, "Notice of Allowance," dated Nov. 21, 2018, 6 pages (not attached).

(Continued)

*Primary Examiner* — Yara B Green
(74) *Attorney, Agent, or Firm* — Kilpatrick Townsend & Stockton LLP

(57) ABSTRACT

Methods and devices are disclosed for the imaging of a biological sample with a top-down camera and a side-view camera. A biological sample is held on an imaging stage that is capable of rotation in two orthogonal axes. The top-down and side-view cameras can record a series of images of the sample using multiple imaging modalities at different rotational positions of the imaging stage. The top-down camera can be translated along its optical axis to affect the camera zoom and influence the resolution and field of view of the recorded images. Fluorescence excitation light sources can be positioned proximate to each of the top-down and side-view cameras to provide substantially uniform illumination of the sample for imaging with each camera.

20 Claims, 9 Drawing Sheets

(56) References Cited

U.S. PATENT DOCUMENTS

| | | |
|---|---|---|
| 5,812,265 A | 9/1998 | Hoshiyama |
| 5,959,295 A | 9/1999 | Braun |
| 6,165,170 A | 12/2000 | Wynne et al. |
| 6,172,373 B1 | 1/2001 | Hara et al. |
| 6,356,272 B1 | 3/2002 | Matsumoto et al. |
| RE37,913 E | 11/2002 | Nishi |
| 6,711,433 B1 | 3/2004 | Geiger et al. |
| 7,218,393 B2 | 5/2007 | Sharpe et al. |
| 7,286,232 B2 | 10/2007 | Bouzid et al. |
| 7,453,456 B2 | 11/2008 | Petrov et al. |
| 7,505,124 B2 | 3/2009 | Kreckel et al. |
| 7,551,711 B2 | 6/2009 | Sarment et al. |
| 7,715,523 B2 | 5/2010 | Lafferty et al. |
| 7,929,743 B2 | 4/2011 | Khorasani et al. |
| 8,115,918 B2 | 2/2012 | Zavislan et al. |
| 8,220,415 B2 | 7/2012 | Lamb et al. |
| 8,503,602 B2 | 8/2013 | Lafferty et al. |
| 8,741,232 B2 | 6/2014 | Baysal et al. |
| 8,754,384 B1 | 6/2014 | Persoon et al. |
| 8,851,017 B2 | 10/2014 | Lamb et al. |
| 8,892,192 B2 | 11/2014 | Cuccia et al. |
| 9,053,563 B2 | 6/2015 | Embrey et al. |
| 9,557,281 B2 | 1/2017 | Yang et al. |
| 9,632,187 B2 | 4/2017 | Poon et al. |
| 2003/0078477 A1 | 4/2003 | Kang et al. |
| 2004/0101088 A1 | 5/2004 | Sabol et al. |
| 2005/0046840 A1 | 3/2005 | Kusuzawa et al. |
| 2005/0227374 A1 | 10/2005 | Cunningham et al. |
| 2006/0072123 A1 | 4/2006 | Wilson et al. |
| 2006/0250518 A1 | 11/2006 | Nilson et al. |
| 2006/0253035 A1 | 11/2006 | Stern |
| 2007/0121099 A1 | 5/2007 | Matsumoto et al. |
| 2007/0276184 A1 | 11/2007 | Okawa |
| 2008/0077019 A1 | 3/2008 | Xiao et al. |
| 2008/0297890 A1 | 12/2008 | Natori et al. |
| 2008/0312540 A1 | 12/2008 | Ntziachristos |
| 2009/0011386 A1 | 1/2009 | Eiff et al. |
| 2009/0018451 A1* | 1/2009 | Bai ............... A61B 5/0073 600/476 |
| 2009/0032731 A1 | 2/2009 | Kimura et al. |
| 2009/0129543 A1 | 5/2009 | Le Gros et al. |
| 2009/0192358 A1 | 7/2009 | Jaffer et al. |
| 2009/0208072 A1* | 8/2009 | Seibel ............ G01N 21/4795 382/128 |
| 2009/0234225 A1 | 9/2009 | Martin et al. |
| 2009/0250631 A1 | 10/2009 | Feke et al. |
| 2010/0309548 A1* | 12/2010 | Power ............ G02B 21/008 359/385 |
| 2011/0116694 A1 | 5/2011 | Gareau et al. |
| 2011/0135190 A1 | 6/2011 | Maad |
| 2011/0229023 A1 | 9/2011 | Jones et al. |
| 2012/0049087 A1 | 3/2012 | Choi et al. |
| 2012/0049088 A1 | 3/2012 | Klose |
| 2012/0065518 A1 | 3/2012 | Mangoubi et al. |
| 2012/0105600 A1 | 5/2012 | Meyer et al. |
| 2012/0182411 A1 | 7/2012 | Nakatsuka et al. |
| 2012/0194663 A1 | 8/2012 | Haisch et al. |
| 2012/0206577 A1 | 8/2012 | Guckenberger et al. |
| 2012/0302880 A1 | 11/2012 | Tian et al. |
| 2012/0312957 A1 | 12/2012 | Loney et al. |
| 2013/0027516 A1 | 1/2013 | Hart |
| 2013/0135081 A1 | 5/2013 | McCloskey et al. |
| 2014/0125790 A1 | 5/2014 | Mackie et al. |
| 2014/0140594 A1 | 5/2014 | Mahadevan-Jansen et al. |
| 2014/0163388 A1 | 6/2014 | Sasayama et al. |
| 2014/0276008 A1 | 9/2014 | Steinbach et al. |
| 2014/0294247 A1 | 10/2014 | Sirault |
| 2014/0346359 A1 | 11/2014 | Holliday |
| 2014/0349337 A1 | 11/2014 | Dasari et al. |
| 2014/0378843 A1 | 12/2014 | Valdes et al. |
| 2015/0000410 A1 | 1/2015 | Grimard et al. |
| 2015/0008337 A1* | 1/2015 | Shimizu ............ G01N 21/59 250/458.1 |
| 2015/0022824 A1 | 1/2015 | Babayoff |
| 2015/0062153 A1 | 3/2015 | Mihalca et al. |
| 2015/0073213 A1 | 3/2015 | Khait et al. |
| 2015/0098126 A1 | 4/2015 | Keller et al. |
| 2015/0105283 A1 | 4/2015 | Hollman-Hewgley et al. |
| 2015/0359413 A1 | 12/2015 | Rainis |
| 2016/0187199 A1 | 6/2016 | Brunk et al. |
| 2016/0245753 A1 | 8/2016 | Wang |
| 2016/0377545 A1 | 12/2016 | Wang |
| 2017/0059487 A1 | 3/2017 | Wang |
| 2017/0176338 A1* | 6/2017 | Wu ..................... G06T 7/90 |
| 2017/0309063 A1 | 10/2017 | Wang |
| 2017/0336706 A1 | 11/2017 | Wang |
| 2017/0367582 A1 | 12/2017 | Wang |
| 2018/0020920 A1* | 1/2018 | Ermilov ............ A61B 5/0035 600/317 |
| 2018/0140197 A1 | 5/2018 | Wang et al. |
| 2018/0180550 A1* | 6/2018 | Franjic ............ G01B 9/02091 |

FOREIGN PATENT DOCUMENTS

| | | |
|---|---|---|
| CN | 103082997 | 10/2015 |
| DE | 102011104216 | 12/2012 |
| GB | 2514125 | 11/2014 |
| KR | 20130096910 | 9/2013 |
| WO | 2006113908 | 10/2006 |
| WO | 2007030424 | 3/2007 |
| WO | 2009115061 | 9/2009 |
| WO | 2013166497 | 11/2013 |
| WO | 2016014252 | 1/2016 |
| WO | 2016073569 | 5/2016 |
| WO | 2016100214 | 6/2016 |
| WO | 2016137899 | 9/2016 |
| WO | 2016210340 | 12/2016 |
| WO | 2017184940 | 10/2017 |
| WO | 2017200801 | 11/2017 |
| WO | 2017223378 | 12/2017 |
| WO | 2018098162 | 5/2018 |

OTHER PUBLICATIONS

EP16756129.9, "Partial European Search Report," dated Oct. 29, 2018, 17 pages.
Badawi et al., Real-Time Tissue Assessment During Surgical Procedures, UC David Office of Research, Tech ID: 24307.
Orpheus Medical, Clinical Video Management and Visible Light Documentation, Slideshow dated Feb. 3, 2016. The Examiner's attention is directed to slide 11.
International Search Report for PCT/US2018/027978 dated Jul. 12, 2018, 5 pages.
Sturm et al., "CopyMe3D: Scanning and Printing Persons in 3D", Medical Image Computing and Computer-Assisted Intervention—Miccai 2015: 18th International Conference, Munich, Germany, Sep. 3, 2013, pp. 405-414.
PCT/US2017/031740, "International Preliminary Report on Patentability", dated Nov. 29, 2018, 18 pages.
PCT/US2017/038860, "International Preliminary Report on Patentability", dated Jan. 3, 2019, 8 pages.
"Arctec Eva Fast Handheld 3D Scanner for Professionals", http://www.artec3d.com/hardware/artec-evat/, retrieved from the internet Apr. 19, 2016, 6 pages.
"Optical Scatter Imaging System for Surgical Specimen Margin Assessment During Breast Conserving Surgery", Project Information NIH Research Portfolio Online Reporting Tools, Project No. 1R01CA192803-01, 2 pages.
Bioptics Inc., "BioVision Digital Specimen Radiography (DSR) System", Premarket Notification 510(k) Summary, May 2009, 8 pages.
Fang et al., "Combined Optical and X-ray Tomosynthesis Breast Imaging", Radiology, vol. 258, No. 1, Jan. 2011, pp. 89-97.
Faxitron Bioptics LLC , "BioVision Surgical Specimen Radiography System", http://www.faxitron.com/medical/products/biovision.html, retrieved from the internet Apr. 26, 2016, 2 pages.
Faxitron Bioptics LLC, "PathVision", http://www.faxitron.com/medical/products/pathvision.html, retrieved from the internet Apr. 26, 2016, 2 pages.

(56) References Cited

OTHER PUBLICATIONS

Lamberts et al., "Tumor-specific uptake of fluorescent bevacizumab-IRDye800CW microdosing in patients with primary breast cancer: a phase I feasibility study", Clinical Cancer Research, Personalized Medicine and Imaging, American Association for Cancer Research, 2016, 41 pages.
Lee et al., "Fusion of coregistered cross-modality images using a temporally alternating display method", Medical & Biological Engineering & Computing, Springer, vol. 38, No. 2, Mar. 1, 2000, pp. 127-132.
International Search Report and Written Opinion dated Jun. 23, 2016 for PCT/US2016/018972, 1 page.
International Search Report and Written Opinion dated Sep. 13, 2016 for PCT/US2016/039382, 2 pages.
International Search Report and Written Opinion dated Sep. 22, 2017 for PCT/US2017/028769, 2 pages.
International Search Report and Written Opinion dated Sep. 19, 2017 for PCT/US2017/031740, 3 pages.
International Search Report and Written Opinion dated Sep. 22, 2017 for PCT/US2017/038860, 3 pages.
International Search Report and Written Opinion dated Feb. 8, 2018 for PCT/US2017/062812, 3 pages.
Perkin Elmer, "Every Cancer Tells a Story If You Have the Tools to Read It", http://go.perkinelmer.com/webmail/32222/179460051/9c4865b118d5295e96e973a5b6c28bad, 2 pages.
Tomowave Laboratories, "Imaging Modules", http://www.tomowave.com/imagingmodules.html, retrieved from the internet, 1 page.
Wu et al., "Rotational imaging optical coherence tomography for full-body mouse embryonic imaging", Journal of Biomedical Optics, vol. 21, No. 2, Feb. 2016, pp. 026002-1-026002-9.

\* cited by examiner

TOP-DOWN AND ROTATIONAL SIDE VIEW BIOPSY SPECIMEN IMAGER AND METHODS

CROSS-REFERENCES TO RELATED APPLICATIONS

The present application claims the benefit of U.S. Provisional Application No. 62/489,921 filed Apr. 25, 2017, the full disclosure of which is incorporated herein by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

Assessment of tumor margin during surgery can be essential to the optimal outcome of many oncologic procedures. Tumor margins are the healthy tissue surrounding the tumor, and more specifically, the distance between the tumor tissue and the edge of the surrounding tissue removed along with the tumor. Ideally, the margins are selected so that the risk of leaving tumor tissue within the patient is low.

Fluorescence image-guided systems can be used in conjunction with a series of imaging agents to visualize tumor margins during surgical procedures for cancer removal. However, in many cancer surgeries deep surgical cavities with closed spaces and hidden linings pose significant challenges. This is particularly true for breast-conserving surgeries and treatments of head and neck cancers. Discharging bio-fluids and small fields of view also can compromise the utility of handheld fluorescence devices for margin assessment at the surgical cavity. Therefore, intra-operative diagnosis on resected surgical samples promises to be a more effective means for margin assessment in many surgical cancer treatment applications. Imaging devices intended for use in the operating room, frozen room, or pathology lab can help in the examination of resected specimens to identify putative disease regions, playing a key role alongside other standard localization methods such as palpation and inspection.

In view of the foregoing, new systems, devices and methods are needed to improve gross examination and margin status. The present invention satisfies these and other needs.

BRIEF SUMMARY

In general, provided herein are devices, methods, computer programs, and systems for imaging a biological sample. The sample is placed on a rotatable imaging stage that is capable of rotating about two orthogonal axes. Two cameras are positioned about the stage to photograph the sample from two different viewpoints. The first of these cameras is a top-down camera that records images of the sample from an overhead angle. The second camera is a side-view camera that records images of the sample from an angle that is generally orthogonal to that of the top-down camera. By using the cameras to capture images of the sample as the stage is moved to different orientations about its axes, a nearly complete scan of the sample can be realized.

The top-down camera can be configured with an optical zoom capability, allowing it to record overhead images of the sample with different fields of view or resolutions. At least one of these fields of view or resolutions can be different from those of the side-view camera. The ability to optically zoom can allow an operator to use the top-down camera to view different regions of interest with different degrees of detail. This can be particularly useful in cases for which the side-view camera and zoomed out top-down camera together record information about the sample as a whole, and the zoomed in top-down camera is used to record information about a specific area of the sample, such as that of a tumor margin. The optical zoom can be accomplished by translating the top-down camera along its optical axis, or by moving or changing the lens assembly of the camera.

The top-down and side-view cameras can each be equipped with sensors or detectors capable of capturing information in two or more imaging modalities. In a preferred embodiment, each of the two cameras can be used to capture reflected light images of the sample, and fluorescence images of the sample. To capture these images, the sample is illuminated with visible light and fluorescence excitation light from two or more light sources. These light sources can be located proximate to the top-down and side-view cameras to increase their effectiveness in providing uniform illumination of the sides of the sample facing each of the two cameras.

One provided apparatus for imaging a biological sample includes a rotatable imaging stage for supporting at least a portion of a biological sample within an imaging volume. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The apparatus further includes a top-down camera configured to have a depth of focus within the imaging volume, wherein the top-down camera has a top-down optical axis that is substantially parallel to the first rotational axis. The apparatus further includes a top-down translational bearing configured to translate the top-down camera substantially parallel with top-down optical axis. The apparatus further includes a side-view camera configured to have a depth of focus within the imaging volume. The side-view camera has a side-view optical axis that forms an angle with the first rotational axis, wherein the angle is within the range from 45 degrees to 135 degrees. The apparatus further includes a visible light source configured to illuminate the imaging volume. The apparatus further includes a fluorescence excitation light source configured to illuminate the imaging volume.

In some embodiments, the angle between the side-view optical axis and the first rotational axis is within the range from 70 degrees to 110 degrees. In some embodiments, the side-view optical axis substantially orthogonal to the first rotational axis.

In some embodiments, the apparatus further includes a computer processor operatively connected with a machine-readable non-transitory medium embodying information indicative of instructions for causing the computer processor to perform operations that can include starting and stopping illumination of the imaging volume by the visible light source. The operations can further include beginning and ending illumination of the imaging volume by the fluorescence excitation light source. The operations can further include rotating the rotatable imaging stage to two or more positions around at least one of the first rotational axis and the second rotational axis. The operations can further include recording, using the top-down camera and the side-view camera, reflected light images of the biological sample with the rotatable imaging stage at the two or more positions while the imaging volume is illuminated by the visible light source. The operations can further include collecting, using the top-down camera and the side-view camera, fluorescence images of the biological sample with the rotatable imaging stage at the two or more positions while the imaging volume is illuminated by the fluorescence excitation light source. The operations can further include constructing a three-dimensional reflected light model from the reflected light images recorded with the rotatable imaging stage at the two or more positions. The operations can further include constructing a three-dimensional fluorescence model from the fluorescence images collected with the rotatable imaging stage at the two or more positions. The operations can further include rendering an image produced from the reflected light model and the fluorescence model, wherein the reflected light model and the fluorescence model are co-registered in three-dimensional space.

In some embodiments, the fluorescence excitation light source comprises two or more lasers. In some embodiments, the fluorescence excitation light source comprises a filtered LED light. In some embodiments, the apparatus further includes a light-tight housing enclosing the rotatable imaging stage, the top-down camera, the top-down translational bearing, the side-view camera, the visible light source, and the fluorescence excitation light source. In some embodiments, the apparatus further includes a top-down active cooling system connected with the top-down camera. In some embodiments, the apparatus further includes a side-view active cooling system connected with the side-view camera.

Another provided apparatus for imaging a biological sample includes a rotatable imaging stage for supporting at least a portion of a biological sample within an imaging volume. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The apparatus further includes a top-down camera configured to have a depth of focus within the imaging volume. The top-down camera has a top-down optical axis that is substantially parallel to the first rotational axis. The apparatus further includes a side-view camera configured to have a depth of focus within the imaging volume. The side-view camera has a side-view optical axis that forms an angle with the first rotational axis, wherein the angle is within the range from 45 degrees to 135 degrees. The apparatus further includes a visible light source configured to illuminate the imaging volume. The apparatus further includes a first fluorescence excitation light source configured to illuminate the imaging volume from a location proximate to the top-down camera. The apparatus further includes a second fluorescence excitation light source configured to illuminate the imaging volume from a location proximate to the side-view camera.

In some embodiments, the angle between the side-view optical axis and the first rotational axis is within the range from 70 degrees to 110 degrees. In some embodiments, the side-view optical axis is substantially orthogonal to the first rotational axis.

In some embodiments, the apparatus further includes a computer processor operatively connected with a machine-readable non-transitory medium embodying information indicative of instructions for causing the computer processor to perform operations. The operations can include starting and stopping illumination of the imaging volume by the visible light source. The operations can further include beginning and ending illumination of the imaging volume by the first fluorescence excitation light source. The operations can further include initiating and terminating illumination of the imaging volume by the second fluorescence excitation light source. The operations can further include rotating the rotatable imaging stage to two or more positions around at least one of the first rotational axis and the second rotational axis. The operations can further include recording, using the top-down camera and the side-view camera, reflected light images of the biological sample with the rotatable imaging stage at the two or more positions while the imaging volume is illuminated by the visible light source. The operations can further include collecting, using the top-down camera, first fluorescence images of the biological sample with the rotatable imaging stage at the two or more positions while the imaging volume is illuminated by the first fluorescence excitation light source. The operations can further include collecting, using the side-view camera, second fluorescence images of the biological sample with the rotatable imaging stage at the two or more positions while the imaging volume is illuminated by the second fluorescence excitation light source. The operations can further include constructing a three-dimensional reflected light model from the reflected light images recorded with the rotatable imaging stage at the two or more positions. The operations can further include constructing a three-dimensional fluorescence model from the first and the second fluorescence images collected with the rotatable imaging stage at the two or more positions. The operations can further include rendering an image produced from the reflected light model and the fluorescence model, wherein the reflected light model and the fluorescence model are co-registered in three-dimensional space.

In some embodiments, the first and second fluorescence excitation light sources each comprise two or more lasers. In some embodiments, the first and second fluorescence excitation light sources each comprise a filtered LED light. In some embodiments, the first fluorescence excitation light source is configured to illuminate the imaging volume with a first fluorescence excitation light beam having a first fluorescence excitation light wavelength. In some embodiments, the second fluorescence excitation light source is configured to illuminate the imaging volume with a second fluorescence excitation light beam having a second fluorescence excitation light wavelength, wherein the second fluorescence excitation wavelength is different from the first fluorescence excitation wavelength.

Also provided are methods for imaging a biological sample. One provided method includes starting illumination of a biological sample with visible light. The biological sample is within an imaging volume and is supported by a rotatable imaging stage. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The method further includes recording, using a top-down camera and a side-view camera, first reflected light images of the biological sample. The top-down camera has a top-down optical axis that is substantially parallel to the first rotational axis, and the side-view camera has a side-view optical axis that forms an angle with the first rotational axis, wherein the angle is within the range from 45 degrees to 135 degrees. The method further includes stopping illumination of the biological sample with visible light. The method further includes beginning illumination of the biological sample with fluorescence excitation light. The method further includes collecting, using the top-down camera and the side-view camera, first fluorescence images of the biological sample. The method further includes ending illumination of the biological sample with fluorescence excitation light. The method further includes rotating the rotatable imaging stage around at least one of the first rotational axis and the second rotational axis. The method further includes, subsequent to the rotating, starting illumination of the biological sample with visible light. The method further includes subsequent to the rotating, recording, using the top-down camera and the side-view camera, second reflected light images of the biological sample. The method further includes subsequent to the rotating, stopping illumination of the biological sample with visible light. The method further includes subsequent to the rotating, beginning illumination of the biological sample with fluorescence excitation light. The method further includes subsequent to the rotating, collecting, using the top-down camera and the side-view camera, second fluorescence images of the biological sample. The method further includes subsequent to the rotating, ending illumination of the biological sample with fluorescent excitation light. The method further includes translating, using a top-down translational bearing, the top-down camera substantially parallel to the top-down optical axis.

In some embodiments, the angle between the side-view optical axis and the first rotational axis is within the range from 70 degrees to 110 degrees. In some embodiments, the side-view optical axis is substantially orthogonal to the first rotational axis.

In some embodiments, the method further includes constructing a three-dimensional reflected light model from the first and second reflected light images. In some embodiments, the method further includes constructing a three-dimensional fluorescence model from the first and second fluorescence images. In some embodiments, the method further includes rendering an image produced from the reflected light model and the fluorescence model, wherein the reflected light model and the fluorescence model are co-registered in three-dimensional space.

In some embodiments, the beginning of illumination of the biological sample with fluorescence excitation light includes illuminating the biological sample with two or more lasers. In some embodiments, the beginning of illumination of the biological sample with fluorescence excitation light comprises illuminating the biological sample with a filtered LED light.

Another provided method for imaging a biological sample includes starting illumination of a biological sample with visible light. The biological sample is within an imaging volume and is supported by a rotatable imaging stage. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The method further includes recording, using a top-down camera and a side-view camera, first reflected light images of the biological sample. The top-down camera has a top-down optical axis that is substantially parallel to the first rotational axis, and the side-view camera has a side-view optical axis that forms an angle with the first rotational axis, wherein the angle is within the range from 45 degrees to 135 degrees. The method further includes stopping illumination of the biological sample with visible light. The method further includes beginning illumination from a first fluorescence excitation light source proximate to the top-down camera to the biological sample. The method further includes collecting, using the top-down camera, a first fluorescence image of the biological sample. The method further includes ending illumination of the biological sample from the first fluorescence excitation light source. The method further includes initiating illumination from a second fluorescence excitation light source proximate to the side-view camera to the biological sample. The method further includes collecting, using the side-view camera, a second fluorescence image of the biological sample. The method further includes terminating illumination of the biological sample from the second fluorescence excitation light source. The method further includes rotating the rotatable imaging stage around at least one of the first rotational axis and the second rotational axis. The method further includes subsequent to the rotating, starting illumination of the biological sample with visible light. The method further includes subsequent to the rotating, recording, using the top-down camera and the side-view camera, second reflected light images of the biological sample. The method further includes subsequent to the rotating, stopping illumination of the biological sample with visible light. The method further includes subsequent to the rotating, beginning illumination from a first fluorescence excitation light source proximate to the top-down camera to the biological sample. The method further includes subsequent to the rotating, collecting, using the top-down camera, a third fluorescence image of the biological sample. The method further includes subsequent to the rotating, ending illumination of the biological sample from the first fluorescence excitation light source. The method further includes subsequent to the rotating, initiating illumination from a second fluorescence excitation light source proximate to the side-view camera to the biological sample. The method further includes subsequent to the rotating, collecting, using the side-view camera, a fourth fluorescence image of the biological sample. The method further includes subsequent to the rotating, terminating illumination of the biological sample from the second fluorescence excitation light source.

In some embodiments, the angle between the side-view optical axis and the first rotational axis is within the range from 70 degrees to 110 degrees. In some embodiments, the side-view optical axis is substantially orthogonal to the first rotational axis.

In some embodiments, the method further includes constructing a three-dimensional reflected light model from the first and second reflected light images. In some embodiments, the method further includes constructing a three-dimensional fluorescence model from the first, second, third, and fourth fluorescence images. In some embodiments, the method further includes rendering an image produced from the reflected light model and the fluorescence model, wherein the reflected light model and the fluorescence model are co-registered in three-dimensional space.

In some embodiments, the first and second fluorescence excitation light sources each comprise two or more lasers. In some embodiments, the first and second fluorescence excitation light sources each comprise a filtered LED light.

Also provided are machine-readable non-transitory media embodying information indicative of instructions for causing a computer processor to perform operations for imaging a biological sample. One provided medium includes instructions for performing operations that include starting illumination of a biological sample with visible light. The biological sample is within an imaging volume and is supported by a rotatable imaging stage. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The operations further include recording, using a top-down camera and a side-view camera, first reflected light images of the biological sample. The top-down camera has a top-down optical axis that is substantially parallel to the first rotational axis, and the side-view camera has a side-view optical axis that forms an angle with the first rotational axis, wherein the angle is within the range from 45 degrees to 135 degrees. The operations further include stopping illumination of the biological sample with visible light. The operations further include beginning illumination of the biological sample with fluorescence excitation light. The operations further include collecting, using the top-down camera and the side-view camera, first fluorescence images of the biological sample. The operations further include ending illumination of the biological sample with fluorescence excitation light. The operations further include rotating the rotatable imaging stage around at least one of the first rotational axis and the second rotational axis. The operations further include subsequent to the rotating, starting illumination of the biological sample with visible light. The operations further include subsequent to the rotating, recording, using the top-down camera and the side-view camera, second reflected light images of the biological sample. The operations further include subsequent to the rotating, stopping illumination of the biological sample with visible light. The operations further include subsequent to the rotating, beginning illumination of the biological sample with fluorescence excitation light. The operations further include subsequent to the rotating, collecting, using the top-down camera and the side-view camera, second fluorescence images of the biological sample. The operations further include subsequent to the rotating, ending illumination of the biological sample with fluorescence exc light. The operations further include translating, using a top-down translational bearing, the top-down camera substantially parallel to the top-down optical axis.

In some embodiments, the angle between the side-view optical axis and the first rotational axis is within the range from 70 degrees to 110 degrees. In some embodiments, the side-view optical axis is substantially orthogonal to the first rotational axis.

In some embodiments, the operations further include constructing a three-dimensional reflected light model from the first and second reflected light images. In some embodiments, the operations further include constructing a three-dimensional fluorescence model from the first and second fluorescence images. In some embodiments, the operations further include rendering an image produced from the reflected light model and the fluorescence model, wherein the reflected light model and the fluorescence model are co-registered in three-dimensional space.

In some embodiments, the beginning of illumination of the biological sample with fluorescence excitation light includes illuminating the biological sample with two or more lasers. In some embodiments, the beginning of illumination of the biological sample with fluorescence excitation light includes illuminating the biological sample with a filtered LED light.

Another provided machine-readable non-transitory medium includes instructions for imaging a biological sample that include starting illumination of a biological sample with visible light. The biological sample is within an imaging volume and is supported by a rotatable imaging stage. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The operations further include recording, using a top-down camera and a side-view camera, first reflected light images of the biological sample. The top-down camera has a top-down optical axis that is substantially parallel to the first rotational axis, and the side-view camera has a side-view optical axis that forms an angle with the first rotational axis, wherein the angle is within the range from 45 degrees to 135 degrees. The operations further include stopping illumination of the biological sample with visible light. The operations further include beginning illumination from a first fluorescence excitation light source proximate to the top-down camera to the biological sample. The operations further include collecting, using the top-down camera, a first fluorescence image of the biological sample. The operations further include ending illumination of the biological sample from the first fluorescence excitation light source. The operations further include initiating illumination from a second fluorescence excitation light source proximate to the side-view camera to the biological sample. The operations further include collecting, using the side-view camera, a second fluorescence image of the biological sample. The operations further include terminating illumination of the biological sample from the second fluorescence excitation light source. The operations further include rotating the rotatable imaging stage around at least one of the first rotational axis and the second rotational axis. The operations further include subsequent to the rotating, starting illumination of the biological sample with visible light. The operations further include subsequent to the rotating, recording, using the top-down camera and the side-view camera, second reflected light images of the biological sample. The operations further include subsequent to the rotating, stopping illumination of the biological sample with visible light. The operations further include subsequent to the rotating, beginning illumination from a first fluorescence excitation light source proximate to the top-down camera to the biological sample. The operations further include subsequent to the rotating, collecting, using the top-down camera, a third fluorescence image of the biological sample. The operations further include subsequent to the rotating, ending illumination of the biological sample from the first fluorescence excitation light source. The operations further include subsequent to the rotating, initiating illumination from a second fluorescence excitation light source proximate to the side-view camera to the biological sample. The operations further include subsequent to the rotating, collecting, using the side-view camera, a fourth fluorescence image of the biological sample. The operations further include subsequent to the rotating, terminating illumination of the biological sample from the second fluorescence excitation light source.

In some embodiments, the angle between the side-view optical axis and the first rotational axis is within the range from 70 degrees to 110 degrees. In some embodiments, the side-view optical axis is substantially orthogonal to the first rotational axis.

In some embodiments, the operations further include constructing a three-dimensional reflected light model from the first and second reflected light images. In some embodiments, the operations further include constructing a three-dimensional fluorescence model from the first, second, third, and fourth fluorescence images. In some embodiments, the operations further include rendering an image produced from the reflected light model and the fluorescence model, wherein the reflected light model and the fluorescence model are co-registered in three-dimensional space.

In some embodiments, the first and second fluorescence excitation light sources each include two or more lasers. In some embodiments, the first and second fluorescence excitation light sources each include a filtered LED light.

Also provided are computer systems for imaging biological samples, the systems including at least one processor and a memory operatively connected with the at least one processor. One provided computer system includes a processor executing instructions from the memory including program code for starting illumination of a biological sample with visible light. The biological sample is within an imaging volume and is supported by a rotatable imaging stage. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The instructions further include program code for recording, using a top-down camera and a side-view camera, first reflected light images of the biological sample. The top-down camera has a top-down optical axis that is substantially parallel to the first rotational axis. The side-view camera has a side-view optical axis that forms an angle with the first rotational axis, wherein the angle is within the range from 45 degrees to 135 degrees. The instructions further include program code for stopping illumination of the biological sample with visible light. The instructions further include program code for beginning illumination of the biological sample with fluorescence excitation light. The instructions further include program code for collecting, using the top-down camera and the side-view camera, first fluorescence images of the biological sample. The instructions further include program code for ending illumination of the biological sample with fluorescent excitation light. The instructions further include program code for rotating the rotatable imaging stage around at least one of the first rotational axis and the second rotational axis. The instructions further include program code for recording, using the top-down camera and the side-view camera, second reflected light images of the biological sample. The instructions further include program code for collecting, using the top-down camera and the side-view camera, second fluorescence images of the biological sample. The instructions further include program code for translating, using a top-down translational bearing, the top-down camera substantially parallel to the top-down optical axis.

In some embodiments, the angle between the side-view optical axis and the first rotational axis is within the range from 70 degrees to 110 degrees. In some embodiments, the side-view optical axis is substantially orthogonal to the first rotational axis.

In some embodiments, the instructions further include program code for constructing a three-dimensional reflected light model from the first and second reflected light images. In some embodiments, the instructions further include program code for constructing a three-dimensional fluorescence model from the first and second fluorescence images. In some embodiments, the instructions further include program code for rendering an image produced from the reflected light model and the fluorescence model, wherein the reflected light model and the fluorescence model are co-registered in three-dimensional space.

In some embodiments, the beginning of illumination of the biological sample with fluorescence excitation light includes illuminating the biological sample with two or more lasers. In some embodiments, the beginning of illumination of the biological sample with fluorescence excitation light includes illuminating the biological sample with a filtered LED light.

Another provided computer system includes a processor executing instructions from the memory including program code for starting illumination of a biological sample with visible light. The biological sample is within an imaging volume and is supported by a rotatable imaging stage. The rotatable imaging stage is mechanically connected to a first rotary bearing having a first rotational axis configured to project through the imaging volume. The rotatable imaging stage is also mechanically connected to a second rotary bearing having a second rotational axis configured to project through the imaging volume. The second rotational axis is substantially orthogonal to the first rotational axis. The instructions further include program code for recording, using a top-down camera and a side-view camera, first reflected light images of the biological sample. The top-down camera has a top-down optical axis that is substantially parallel to the first rotational axis. The side-view camera has a side-view optical axis that forms an angle with the first rotational axis, wherein the angle is within the range from 45 degrees to 135 degrees. The instructions further include program code for stopping illumination of the biological sample with visible light. The instructions further include program code for beginning illumination from a first fluorescence excitation light source proximate to the top-down camera to the biological sample. The instructions further include program code for collecting, using the top-down camera, a first fluorescence image of the biological sample. The instructions further include program code for ending illumination of the biological sample from the first fluorescence excitation light source. The instructions further include program code for initiating illumination from a second fluorescence excitation light source proximate to the side-view camera to the biological sample. The instructions further include program code for collecting, using the side-view camera, a second fluorescence image of the biological sample. The instructions further include program code for terminating illumination of the biological sample from the second fluorescence excitation light source. The instructions further include program code for rotating the rotatable imaging stage around at least one of the first rotational axis and the second rotational axis. The instructions further include program code for recording, using the top-down camera and the side-view camera, second reflected light images of the biological sample. The instructions further include program code for collecting, using the top-down camera, a third fluorescence image of the biological sample. The instructions further include program code for collecting, using the side-view camera, a fourth fluorescence image of the biological sample.

In some embodiments, the angle between the side-view optical axis and the first rotational axis is within the range from 70 degrees to 110 degrees. In some embodiments, the side-view optical axis is substantially orthogonal to the first rotational axis.

In some embodiments, the instructions further include program code for constructing a three-dimensional reflected light model from the first and second reflected light images. In some embodiments, the instructions further include program code for constructing a three-dimensional fluorescence model from the first, second, third, and fourth fluorescence images. In some embodiments, the instructions further include program code for rendering an image produced from the reflected light model and the fluorescence model, wherein the reflected light model and the fluorescence model are co-registered in three-dimensional space.

In some embodiments, the first and second fluorescence excitation light sources each comprise two or more lasers. In some embodiments, the first and second fluorescence excitation light sources each comprise a filtered LED light.

For each of the above embodiments, reference to features included in devices, methods, or systems indicate that those devices, methods, or systems can comprise, consist of, or consist essentially of each of the referenced features.

The phrase "substantially" is used herein to modify a direction and indicate a defined range about that direction. A reference to a feature being substantially in a given direction generally indicates that the feature is at an angle within 10% of the direction as measured in an angular coordinate system. For example, if a first direction is substantially parallel to a second direction, then the first direction is at least within 30%, 25%, 20%, 15%, 10%, 9%, 8%, 7%, 6%, 5%, 4%, 3%, 2%, or 1% of the second direction. Similarly, if a first direction is substantially orthogonal to a second direction, the first direction is at least within 30%, 25%, 20%, 15%, 10%, 9%, 8%, 7%, 6%, 5%, 4%, 3%, 2%, or 1% of a third direction at a right angle to the second direction. Directions that are not exactly orthogonal or parallel to one another can have offset angles due to machining tolerances or due to requirements for reducing reflections, simplifying mechanical designs, or other reasons.

DETAILED DESCRIPTION

Embodiments of the present invention relate in part to imaging functions, such as those, for example, used for surgical or biopsy imaging. The provided methods and systems generally use at least two cameras to photograph a biological sample from two different vantage points that are generally orthogonal to one another. A top-down camera provides an overhead view of the biological sample as a side-view camera provides a lateral view. The top-down camera can also be optically zoomed to provide a more detailed analysis of specified regions of interest on the sample while the side-view camera continues to provide a broader overview of the sample. This can provide a technical advantage to applications in which higher-resolution imaging is desired without sacrificing speed or a larger field of view. As an example, a surgeon can image a tumor sample as a whole while verifying in fine detail if a tumor removal margin is sufficient. The combination of different viewpoints, resolutions, and fields of view can also provide an advantage to applications in which recorded emitted fluorescence is relatively dim, with fluorescent features difficult to distinguish.

Figure 1:
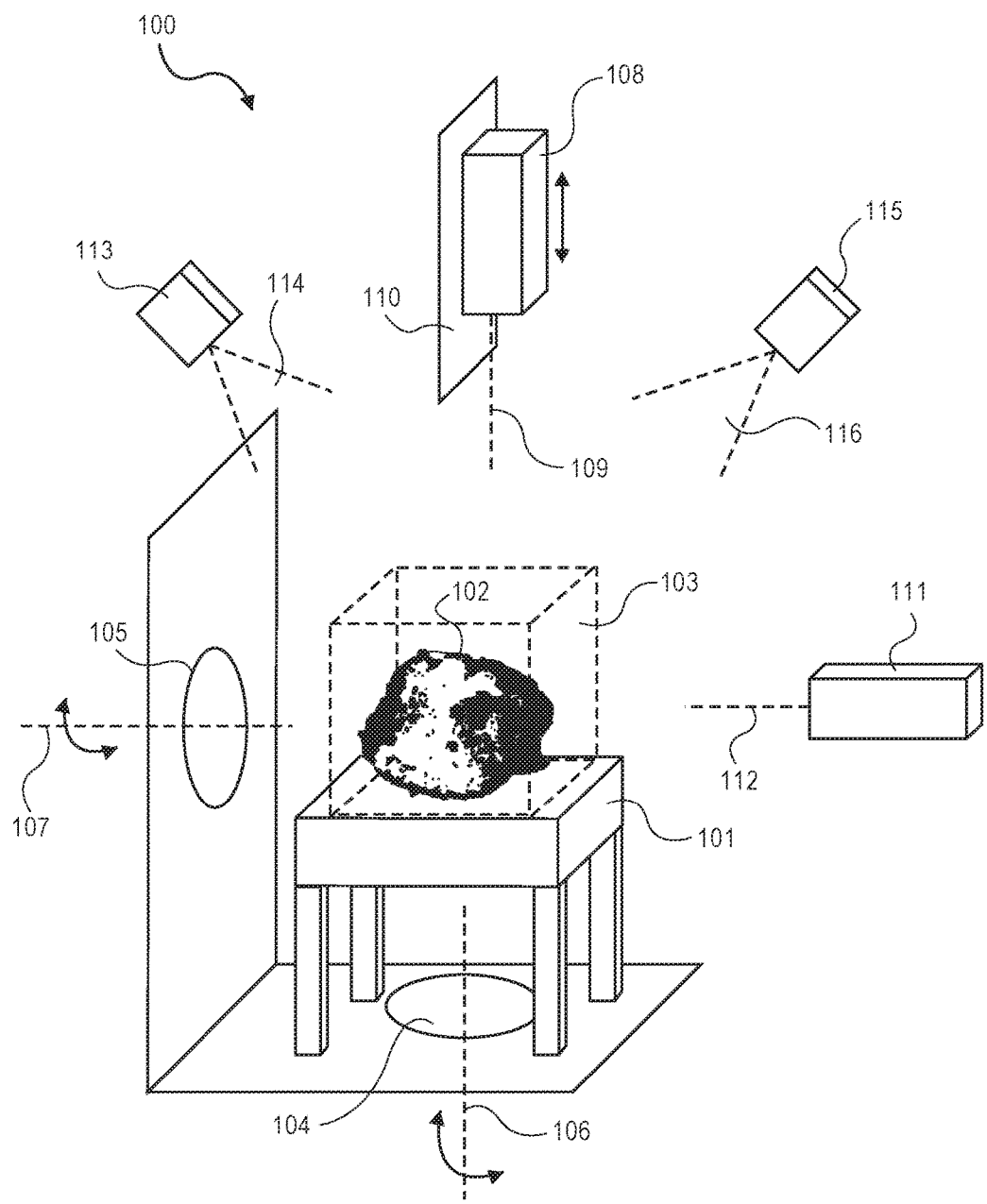
FIG. 1 is an illustration of an imaging system having a top-down translational bearing configured to translate a top-down camera in accordance with an embodiment.

FIG. 1 illustrates one embodiment as a descriptive example. Shown is an imaging apparatus 100 that includes a rotatable imaging stage 101. The stage supports a biological sample 102, wherein at least a portion of the sample is within an imaging volume 103. The stage is mechanically connected to a first rotary bearing 104 and a second rotary bearing 105. The first rotary bearing has a first rotational axis 106 that is configured to project through the imaging volume, and the second rotary bearing has a second rotational axis 107 that is also configured to project through the imaging volume. The first and second rotational axes are substantially orthogonal to one another.

The imaging apparatus 100 also includes a top-down camera 108 that is configured to have a depth of focus within the imaging volume 103. The top-down camera has a top-down optical axis 109 that is substantially parallel to the first rotational axis 106 of the first rotational bearing 104. The top-down camera is mechanically connected to a translational bearing 110 configured to translate the top-down camera along a direction substantially parallel to the top-down optical axis. The imaging apparatus also includes a side-view camera 111 that is configured to have a depth of focus within the imaging volume. The side-view camera has a side-view optical axis 112 that is substantially orthogonal to the first rotational axis of the first rotational bearing and substantially parallel to the second rotational axis 107 of the second rotational bearing 105.

The imaging apparatus 100 also includes a visible light source 113. The visible light source is configured to illuminate the imaging volume 103 with visible light 114. The apparatus also includes a fluorescence excitation light source 115. The fluorescence light source is configured to illuminate the imaging volume with fluorescence excitation light 116.

The rotatable imaging stage can comprise a transparent portion, such as a window. The window can be transparent at the working wavelengths for visible light and fluorescence excitation light. The transparent portion can further be transparent to reflected light and fluorescence emission light. To accommodate a large size sample, the window can be configured to have a shape that is wider than either the projection size of the imaging volume or the footprint of the target sample. A circle on the window can be used to mark the border of a suggested imaging area.

The material of the transparent portion can be, for example and without limitation, borosilicate-based glass, acrylic, or other transparent material. The surface could be treated or coated for optical or surface functional requirements. Non-limiting examples of these treatments include those providing anti-reflection, transparency, absorption, hydrophobic, or hydrophilic properties to the surface.

The rotatable imaging stage can further comprise one or more marks. The marks can be regularly spaced or irregularly spaced. The marks can be configured to provide reference scales to users of the apparatus. The marks can also provide references to a computer processor used to analyze and manipulate images recorded of the sample within the imaging volume. In some embodiments, the marks comprise an opaque material. The radiopaque material can comprise a polymer or a metal.

The biological sample can comprise material removed from a subject. The subject is typically a human, but also can be another animal. The subject can be, for example, rodent, canine, feline, equine, ovine, porcine, or another primate. The subject can be a patient suffering from a disease. In some embodiments, the subject is a cancer patient. In certain aspects, the biological sample comprises a tumor, such as tumor tissue or cells. In certain aspects, the biological sample comprises a peripheral biopsy of a tissue sample previously removed. In another aspect, the biological sample is tumor tissue such as a breast core biopsy. The biological sample size can be as small as a tissue slice or can have a larger volume.

The biological sample can include a fluorescent dye or group. In one aspect, the fluorescent group is a near-infrared (NIR) fluorophore that emits light in the wavelength range of between about 650 to about 1400 nm. Use of NIR fluorescence technology with the provided embodiments can be advantageous as NIR fluorescence can substantially eliminate or reduce background signals from the auto fluorescence of tissue. Another benefit to NIR fluorescence technology is that the scattering of light from the excitation source is greatly reduced since scattering intensity is proportional to the inverse fourth power of the wavelength. Low background fluorescence and low scattering can result in a high signal-to-noise ratio, which can be greatly desired for highly sensitive detection. Furthermore, the optical transparency of biological tissues to light in the NIR-I region (650 nm to 990 nm) or NIR-II region (between about 1000 nm and 1700) makes NIR fluorescence a valuable technology for imaging and subcellular detection applications that require the transmission of light through biological components. In certain aspects, the fluorescent dye or group is a fluorophore emitting light in the visible light range from 400 nm to 650 nm.

In certain aspects, the fluorescent dye is preferably selected from the group consisting of IRDye® 800RS, IRDye® 800CW, IRDye® 800, Alexa Fluor® 660, Alexa Fluor® 680, Alexa Fluor® 700, Alexa Fluor® 750, Alexa Fluor® 790, indocyanine green (ICG), Gliolan®, Cy5, Cy5.5, Cy7, DY 676, DY680, DY682, and DY780. In certain aspects, the near infrared group is IRDye® 800CW, IRDye® 800, IRDye® 700DX, IRDye® 700, or Dynomic DY676.

In certain aspects, the fluorescent dye is contacted with the biological sample prior to excising the biological sample from the subject. For example, the dye can be injected or administered to the subject prior to surgery or after surgery. In certain aspects, the dye is conjugated to an antibody, ligand, or targeting moiety having an affinity to a tumor or recognition of a tumor antigen. In certain aspects, the fluorescent dye comprises a targeting moiety. In one aspect, the surgeon "paints" the tumor with the dye. In certain aspects, the fluorescent dye is contacted with the biological sample after excising the biological sample from the subject. In this manner, dye can be contacted to the tissue at the margins.

In some aspects, the targeting molecule is an antibody that binds an antigen such as a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, or an osteosarcoma cell surface antigen.

Fluorophore methods utilize molecules that absorb light of one spectrum and emit light of a different spectrum. To utilize a visible image in combination with a fluorophore (e.g., an infrared or near-infrared fluorophore), care should be taken to ensure that the spectra of light variously absorbed, reflected, and emitted do not significantly overlap to confound differentiation of the components from each other and differentiation of the components from endogenous tissue material. The provided devices and methods utilize a combination of invisible light (e.g., infrared or near-infrared) fluorophores and visible light images to visualize and analyze biological samples.

The imaging volume is defined as the volume formed by the fields of illumination or other electromagnetic radiation, by the depth-of-focus of object lenses, and by the field-of-view of an imaging head. The imaging volume is typically configured such that all cameras, detectors, sensors, and other image capturing elements of the apparatus are tolerant of placement of the sample anywhere within the volume.

The rotatable imaging stage supporting the biological sample within the imaging volume is equipped with rotational motors to control the view angle and position of a sample within the imaging volume. By rotating a sample in two degrees of freedom, the stage can allow an imager to efficiently provide a nearly full-rotation three-dimensional image. The first rotational axis can, for example, provide nearly 360-degree movement along the z-axis (roll) relative to the sample. The second rotational axis can, for example, tilt along the y-axis (pitch) for imaging at different perspectives. Tilting of the sample stage also allows projection views from the top and the bottom of the sample via a transparent window. In some embodiments, the rotational imaging stage can also be moved in an X-Y plane to allow for the registration of the sample to the center of the imaging volume.

Rotational combinations can allow nearly the entire sample to be imaged. To collect pertinent imaging projections along a sample for subsequent three-dimensional reconstruction, the rotational imaging stage can rotate the object in rolling and tilting degrees of freedom. In some embodiments, to provide nearly comprehensive coverage of sample features the rolling angle is in the range of from 7.5 degrees to 45 degrees, depending on the complexity of the sample. In some embodiments, a rolling step of 22.5 degrees and a tilting angle of ±35 degrees offers a nearly full rotation for three-dimensional inspection and imaging of the sample.

Rotation of the imaging stage around one or both of the first and second rotational axis can be accomplished through the use of rotary bearings connected to the stage. Rotary bearings are mechanical elements that provide for rotation about a rotational axis. A rotary bearing can include a hub, axle, or other mechanical element that bears contact between at least two parts and that allows for rotation around the rotational axis. A rotary bearing can include circular tracks and cages for ball bearings, lubricant surfaces, or other friction-reducing implements to facilitate the rotation about the rotational axis. Further descriptions and examples of rotary bearings and rotatable imaging stages suitable for use with the present imaging apparatus can be found in U.S. Patent Application Publication No. US 20017/0059487, which is incorporated herein in its entirety for all purposes.

The imaging apparatus can including a sample handling module or system configured to load samples onto the rotatable imaging stage prior to being imaged, or to remove samples from the rotatable imaging stage subsequent to being imaged. Sample handling systems can include, for example and without limitation, a high-throughput or high-capacity sample carrier or holder, and a conveyor mechanism configured to transport samples from the carrier or holder to the rotatable imaging stage.

The top-down and side-view cameras can each include one or more sensors or lens assemblies configured to capture, collect, or record imaging data or information in one or more imaging modalities. In some embodiments, the top-down camera is configured to collect reflected visible light imaging data, and the side-view camera is configured to collect emitted fluorescence imaging data. In some embodiments, the top-down camera is configured to collect emitted fluorescence imaging data, and the side-view camera is configured to collect reflected visible light imaging data. In a preferred embodiment, the top-down and side-view cameras are each configured to collect both reflected visible light and emitted fluorescence imaging data. Other imaging modalities that are suitable for use with the provided devices, systems, and methods include, but are not limited to, X-ray imaging to visualize tissue density and radiopaque tissue inserts, photoacoustic imaging, thermoacoustic imaging, ultrasonic imaging, and optical coherence tomography (OCT).

The top-down and side-view cameras can have the same or different optical specifications. Optical specifications of the cameras include, without limitation, such features as field of view, viewing angles, imaging depth, light responses and sensitivities, and resolutions. In some embodiments, the top-down camera and the side-view camera are used to photograph different regions of interest on the biological sample at different resolutions. In some embodiments, one of the top-down camera and the side-view camera is used to record a macroscopic image with a large field of view, while other of the cameras is used to record an optically zoomed image with a smaller field of view. The macroscopic image can have a field of view large enough to record imaging data of an entire side, face, or projection of the biological sample. The fields of view of the cameras can be within the range from 1 cm$^2$ to 500 cm$^2$, e.g., from 1 cm$^2$ to 300 cm$^2$, from 50 cm$^2$ to 350 cm$^2$, from 100 cm$^2$ to 400 cm$^2$, from 150 cm$^2$ to 450 cm$^2$, or from 200 cm$^2$ to 500 cm$^2$. The fields of view of the cameras can be within the range from 1 cm$^2$ to 100 cm$^2$, from 100 cm$^2$ to 200 cm$^2$, from 200 cm$^2$ to 300 cm$^2$, from 300 cm$^2$ to 400 cm$^2$, or from 400 cm$^2$ to 500 cm$^2$. The resolutions of the cameras can be within the range from 10 μm to 200 μm, e.g., from 10 μm to 120 μm, from 30 μm to 140 μm, from 50 μm to 160 μm, from 70 μm to 180 μm, or from 90 μm to 200 μm. The resolutions of the cameras can be within the range from 10 μm to 40 μm, from 40 μm to 80 μm, from 80 μm to 120 μm, from 120 μm to 160 μm, or from 160 μm to 200 μm.

Translation of the top-down camera along the top-down optical axis can be accomplished through the use of a translation bearing or linear stage. The translational bearing can include a platform and a base, wherein the top-down camera is mechanically connected to the platform at a substantially fixed position, and the top-down camera and platform move along one axis relative to the base. The translational bearing can also include a guide that substantially restricts movement of the camera and platform to the one dimension of the optical axis. The mechanism of the guide can include, for example and without limitation, one or more ball bearings, recirculating ball bearings, crossed roller bearings, flexures, cylindrical sleeves, or dovetail slides. The top-down camera can move along its optical axis through the use of a slider or mechanical armature.

In some embodiments, the side-view camera is mechanically connected to a translational bearing configured to move the side-view camera along the side-view optical axis. The side-view translational bearing can include any of the elements, mechanisms, and designed described above for the top-down translation bearing. The side-view and top-down translational bearings can be similar or different from one another.

The individual cameras of the imaging apparatus, or the apparatus as a whole, can be used to photograph different regions of interest of the biological sample at different resolutions and with different fields of view. When an individual camera is used to record image data at different resolutions, the camera can be configured to have an optical zoom capability. The optical zoom can include translation of the entire camera or a lens assembly of the camera along the optical axis of the camera. The optical zoom can include replacement of one or more lenses of the camera. Multiple lenses for a camera can be held, for example, in a rotatable turret of lenses configured to selectively position different lenses in the optical axis of the camera between the camera sensor and the imaging volume.

The use of optical zoom with the provided devices and methods can be particularly valuable in cases for which a biological sample should be interrogated in detail. This can be, for example, with a sub-region prepared from a gross sample, or with a small extension site of a pathological feature identified on a primary specimen. In some aspects, it can be beneficial for a surgeon to have access to higher resolution, optically zoomed images of resected tissue to verify adequate removal of tumor margin. The use of optical zoom can also provide significant enhancements to the viewing of fluorescent features that are relatively dim or difficult to distinguish from one another or from background.

The individual cameras of the imaging apparatus or the apparatus as a whole can be used to photograph at different fields of view while maintaining a fixed resolution. In some embodiments, the field of view can be changed by moving the stage about one or both of its rotational axes, photographing multiple individual images as the stage is at multiple positions, and stitching or combining the multiple individual images into a larger composite image having a larger field of view than the individual component images.

Any one or more cameras of the apparatus can have an actively or passively cooled heat exchanger to maintain imaging sensors at low temperatures. The imaging sensors can be charge coupled device imaging sensors. The cooling can prevent optical background noise such as darkness or blooming. Other approaches for improving camera sensitivity to compensate for low light levels of fluorescence can include imaging with a monochrome sensor, long exposure durations, and electronic noise suppression methods. Exemplary camera and optical components are described in U.S. Pat. Nos. 7,286,232, 8,220,415, and 8,851,017.

The imaging apparatus can include a light-tight housing. The effectiveness of some imaging processes, and in particular those that involve fluorescence, can be enhanced by minimizing the effects of light originating from outside of the imaging apparatus or system. A light-tight housing can reduce the amount of this exterior light, which can be prevalent in, for example, a bright operating room environment. The light-tight housing can enclose each of the rotatable imaging stage, the top-down camera, the top-down translational bearing, the side-view camera, the visible light source, and the fluorescence excitation light source. The light-tight housing can also enclose other apparatus elements such as, but not limited to, cooling systems or elements thereof; power sources or elements thereof; electrical wiring; computer systems or elements thereof; communication devices or elements thereof; and sensors of temperature, humidity, light intensity, or other environmental parameters.

The visible light source can be mounted proximate to the imaging volume in order to illuminate the sample with white light or monochrome light. One or more white lights can be used to illuminate the imaging volume. One or more RGB LED lights can be used to illuminate the imaging volume. In some embodiments, the illumination of the biological sample with visible light is performed at one or more wavelengths of about 380 nm to about 700 nm. These wavelengths include, for example, about 380 nm, about 390 nm, about 400 nm, about 425 nm, about 450 nm, about 475 nm, about 500 nm, about 525 nm, about 550 nm, about 575 nm, about 600 nm, about 625 nm, about 650 nm, about 675 nm, or about 700 nm. These wavelengths can occur in combination, such as in broadband white light.

The fluorescence excitation light source can be mounted proximate to the imaging volume in order to illuminate the sample with near-infrared light, fluorescent light, or other electromagnetic radiation. The fluorescence excitation light source can be a wide-band excitation source, or a narrow-band excitation such as a laser diode or filtered LED light. The illumination of the biological sample with fluorescence excitation light from the fluorescence light source can be performed at one or more wavelengths of about 650 nm to about 1400 nm. These wavelengths include, for example, about 700 nm, about 725 nm, about 750 nm, about 775 nm, about 800 nm, about 825 nm, about 850 nm, about 875 nm, about 900 nm, about 910 nm, about 920 nm, about 930 nm, about 940 nm, about 950 nm, about 960 nm, about 970 nm, about 980 nm, about 990 nm, about 1000 nm, about 1100 nm, about 1200 nm, about 1300 nm, and about 1400 nm. These wavelengths can be in the NIR-I or NIR-II wavelength regions. The illumination of the biological sample with fluorescence excitation light from the fluorescence light source can be performed at one or more wavelengths of about 400 nm to about 650 nm. These wavelengths include, for example, about 400 nm, about 425 nm, about 450 nm, about 475 nm, about 500 nm, about 525 nm, about 550 nm, about 575 nm, about 600 nm, about 625 nm, and about 650 nm. The fluorescence excitation light source is in general a light source that is configured to illuminate with light lacking the emission wavelength or wavelengths of the fluorescent materials to be excited.

The fluorescence excitation light source can include two or more lasers. In general, each of the two or more lasers of the fluorescence excitation light source has an operating wavelength that is identical to or substantially identical to the operating wavelength of the other lasers of the fluorescence excitation light source. The fluorescence excitation light source can include two, three, four, five, six, seven, eight, nine, ten, or more than ten lasers. The two or more lasers can be located proximate to one another, illuminating the imaging volume from substantially similar angles relative to the first and second rotational axes of the rotatable imaging stage. In some embodiments, the fluorescence excitation light source includes two lasers. The two or more lasers can be located in substantially different positions, illuminating the imaging volume from substantially different angles relative to the first and second rotational axes of the rotatable imaging stage. In some embodiments, the fluorescence excitation light source includes three lasers. In some embodiments, the fluorescence excitation light sources includes four or more lasers. The imaging apparatus can include two or more fluorescence excitation light sources, each of which can include one or more lasers. In embodiments having two or more fluorescence excitation light sources, each laser of an individual fluorescence excitation light source will generally have the same or substantially the same operating wavelength as the other lasers of the individual fluorescence excitation light source. Lasers of different fluorescence excitation light sources can have operating wavelengths that are different from one another.

The fluorescence excitation light source can include a filtered LED light. The fluorescence excitation light source can include two or more filtered LED lights. The fluorescence excitation light source can include two, three, four, five, six, seven, eight, nine, ten, or more than ten filtered LED lights. The one or more filtered LED lights can be filtered so as to reduce the range or band of wavelengths in the fluorescence excitation light source to a range or band that includes the excitation wavelength or wavelengths of one or more fluorescent materials within the imaging volume. The one or more filtered LED lights can be filtered so as to eliminate a range or band of wavelengths that includes the emission wavelength or wavelengths of one or more fluorescent materials within the imaging volume. The imaging apparatus can include two or more fluorescence excitation light sources, each of which can include one or more filtered LED lights. Each fluorescence excitation light source of the apparatus can emit a similar or different range of wavelength light.

In some embodiments, there are two or more light sources per camera. There can be two, three, four, five, six, seven, eight, nine, ten, or more than ten light sources per camera. All or some of the light sources associated with the top-down camera can be configured or operated to be turned on while all or some of the light sources associated with the side-view camera are configured or operated to be off. All or some of the light sources associated with the side-view camera can be configured or operated to be turned on while all or some of the light sources associated with the top-down camera are configured or operated to be off. All or some of light sources associated with each of the top-down and side-view cameras can be configured or operated to be turned on or off simultaneously.

Different illumination sources for the top-down camera and the side-view camera can have similar or different intensities. The different illumination sources can have similar or different temporal modulations. In some embodiments, an illumination can include both white light and fluorescence excitation light used to alternately illuminate the subject in a modulated fashion. The modulated electromagnetic radiations can differ in amplitude, phase, frequency, or polarization. In some embodiments, different lasers associated with the top-down and side-view cameras are shut off in alternating or interlaced fashion.

In some aspects, one or both of the visible light and fluorescence excitation light sources can change the color, wavelength, or range of wavelengths of lights produced from the sources. In some aspects, one or both of the visible light and fluorescence excitation light sources can change the direction of illumination. The light sources can be configured to project illumination light through optical elements such as one or more lenses, filters, reflecting mirrors, dichroic mirrors, or beam splitters. In some embodiments, a mirror reflects fluorescence excitation light and/or visible light to illuminate the imaging volume, wherein the mirror is located proximate to the top-down camera. In some embodiments, a mirror reflects fluorescence excitation light and/or visible light to illuminate the imaging volume, wherein the mirror is located proximate to the side-view camera. One or both of the light sources can change position or move to change the illumination intensity or illumination area produced from the sources. The movement of the one or more light sources can be connected to or independent from movement of one or both of the top-down and side-view cameras of the imaging apparatus.

Figure 2:
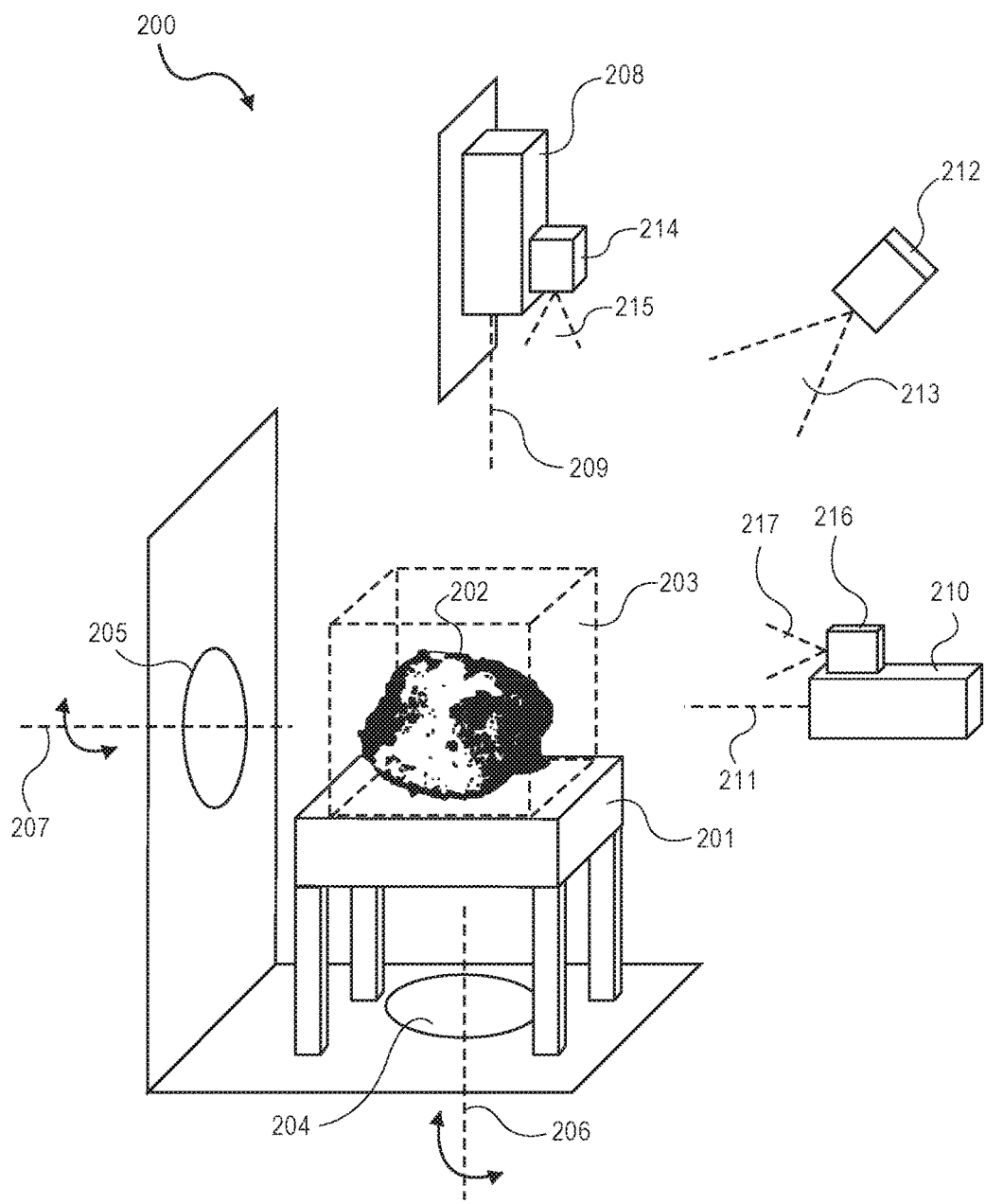
FIG. 2 is an illustration of an imaging system having fluorescence excitation light sources configured to illuminate an imaging volume from locations proximate to top-down and side-view cameras in accordance with an embodiment.

FIG. 2 illustrates an embodiment in which the light sources are proximate to the cameras of the apparatus. Shown is an imaging apparatus 200 that includes a rotatable imaging stage 201. The stage supports a biological sample 202, wherein at least a portion of the sample is within an imaging volume 203. The stage is mechanically connected to a first rotary bearing 204 and a second rotary bearing 205. The first rotary bearing has a first rotational axis 206 that is configured to project through the imaging volume, and the second rotary bearing has a second rotational axis 207 that is also configured to project through the imaging volume. The first and second rotational axes are substantially orthogonal to one another.

The imaging apparatus 200 also includes a top-down camera 208 that is configured to have a depth of focus within the imaging volume 203. The top-down camera has a top-down optical axis 209 that is substantially parallel to the first rotational axis 206 of the first rotational bearing 204. The imaging apparatus also includes a side-view camera 210 that is configured to have a depth of focus within the imaging volume. The side-view camera has a side-view optical axis 211 that is substantially orthogonal to the first rotational axis of the first rotational bearing and substantially parallel to the second rotational axis 207 of the second rotational bearing 205.

The imaging apparatus 200 also includes a visible light source 212. The visible light source is configured to illuminate the imaging volume 203 with visible light 213. The apparatus also includes a first fluorescence excitation light source 214. The first fluorescence excitation light source is configured to illuminate the imaging volume with fluorescence excitation light 215 from a location proximate to the top-down camera 208. The apparatus also includes a second fluorescence excitation light source 216. The second fluorescence excitation light source is configured illuminate the imaging volume with fluorescence excitation light 217 from a location proximate to the side-view camera 210.

In some embodiments, the first and second fluorescence excitation light sources are mechanically connected to top-down and side-view cameras, respectively, as shown in FIG. 2. The first and second fluorescence excitation light sources can move along with the top-down and side-view cameras, respectively, as the cameras are optionally translated along the top-down and side-view optical axes as described above.

In certain aspects, the imaging apparatus also includes one or more mirrors configured to redirect light traveling from the imaging volume to one or both of the top-down camera and the side-view camera. In some embodiments, the one or more mirrors are located and oriented such that the top-down camera is at a position other than directly above the imaging volume, and/or the side-view camera is at a position other than directly to the side of the imaging volume. In these configurations, the term "optical axis" as used herein to describe a camera refers to the axis of light traveling from the imaging volume to the mirror along a path to the camera.

Figure 3:
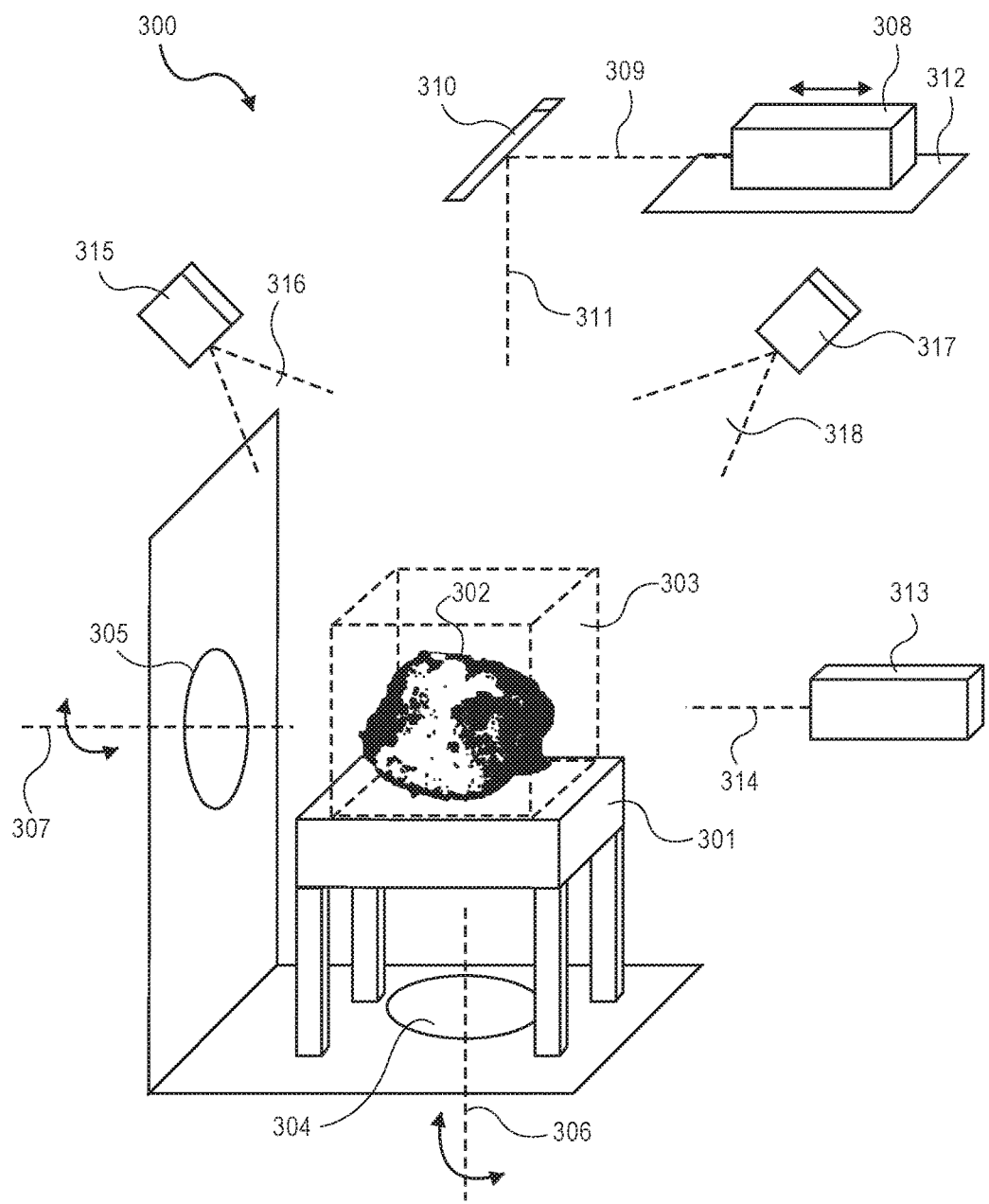
FIG. 3 is an illustration of an imaging system having a mirror configured to redirect light to a top-down camera in accordance with an embodiment.

FIG. 3 illustrates an embodiment in which a mirror reflects light from the imaging volume to the optical path of the top-down camera. Shown is an imaging apparatus 300 that includes a rotatable imaging stage 301. The stage supports a biological sample 302, wherein at least a portion of the sample is within an imaging volume 303. The stage is mechanically connected to a first rotary bearing 304 and a second rotary bearing 305. The first rotary bearing has a first rotational axis 306 that is configured to project through the imaging volume, and the second rotary bearing has a second rotational axis 307 that is also configured to project through the imaging volume. The first and second rotational axes are substantially orthogonal to one another.

The imaging apparatus 300 also includes a top-down camera 308 that has a top-down optical axis 311 and that is configured to have a depth of focus within the imaging volume 303. A mirror 310 reflects light 309 to the top-down camera, wherein the light exits from the imaging volume in a direction substantially parallel to the first rotational axis 306. The top-down camera is mechanically connected to a translational bearing 312 configured to translate the top-down camera with respect to the mirror. The imaging apparatus also includes a side-view camera 313 that is configured to have a depth of focus within the imaging volume. The side-view camera has a side-view optical axis 314 that is substantially orthogonal to the first rotational axis of the first rotational bearing and substantially parallel to the second rotational axis 307 of the second rotational bearing 305.

The imaging apparatus 300 also includes a visible light source 315. The visible light source is configured to illuminate the imaging volume 303 with visible light 317. The apparatus also includes a fluorescence excitation light source 317. The fluorescence excitation light source is configured to illuminate the imaging volume with fluorescence excitation light 318.

In some embodiments, the top-view camera and the side-view camera are the same camera. The camera can be alternatingly repositioned from a side view position to a top-down position. The camera can be mechanically connected to a sliding or rotating bearing or an armature that can move the camera between the top-down and side-view positions. In some embodiments, the camera can rotate or translate from a first orientation in which the camera is directed towards a first system of one or more mirrors to a second orientation in which the camera is directed towards a second system of one or more mirrors. The first mirror system can reflect light from the biological sample substantially parallel to the first rotational axis such that the rotating or translating camera operates as a top-down camera when in the first orientation. The second mirror system can reflect light from the biological sample substantially orthogonal to the first rotational axis such that the rotating or translating camera operates as a side-view camera when in the second orientation.

In some embodiments, a system of one or more mirrors can be alternatingly repositioned such that as the mirror system is in one configuration, light that is emitted or reflected by the biological sample substantially parallel to the first rotational axis is reflected by the mirror system to a single camera. In this way, the single camera operates as a top-down camera with the mirror system in a first configuration, recording or capturing image data of the biological sample along an optical axis substantially parallel to the first rotational axis of the rotatable imaging stage. As the mirror system is positioned in a second configuration, light that is emitted or reflected by the biological sample substantially orthogonal to the first rotational axis is reflected by the mirror system to the single camera. In this way, the single camera operates as a side-view camera with the mirror configuration in a second configuration, recording or capturing image data of the biological sample along an optical axis substantially orthogonal to the first rotational axis of the rotatable imaging stage.

In some embodiments, a system of one or more mirrors can be alternatingly repositioned such that as the mirror system is in one configuration, light that is emitted or reflected by the biological sample substantially parallel to the first rotational axis passes unimpeded by the mirror system to a single camera. In this way, the single camera operates as a top-down camera with the mirror system in a first configuration, recording or capturing image data of the biological sample along an optical axis substantially parallel to the first rotational axis of the rotatable imaging stage. As the mirror system is positioned in a second configuration, light that is emitted or reflected by the biological sample substantially orthogonal to the first rotational axis is reflected by the mirror system to the single camera. In this way, the single camera operates as a side-view camera with the mirror configuration in a second configuration, recording or capturing image data of the biological sample along an optical axis substantially orthogonal to the first rotational axis of the rotatable imaging stage.

In some embodiments, a system of one or more mirrors can be alternatingly repositioned such that as the mirror system is in one configuration, light that is emitted or reflected by the biological sample substantially parallel to the first rotational axis is reflected by the mirror system to a single camera. In this way, the single camera operates as a top-down camera with the mirror system in a first configuration, recording or capturing image data of the biological sample along an optical axis substantially parallel to the first rotational axis of the rotatable imaging stage. As the mirror system is positioned in a second configuration, light that is emitted or reflected by the biological sample substantially orthogonal to the first rotational axis passes unimpeded by the mirror system to the single camera. In this way, the single camera operates as a side-view camera with the mirror configuration in a second configuration, recording or capturing image data of the biological sample along an optical axis substantially orthogonal to the first rotational axis of the rotatable imaging stage.

Figure 4:
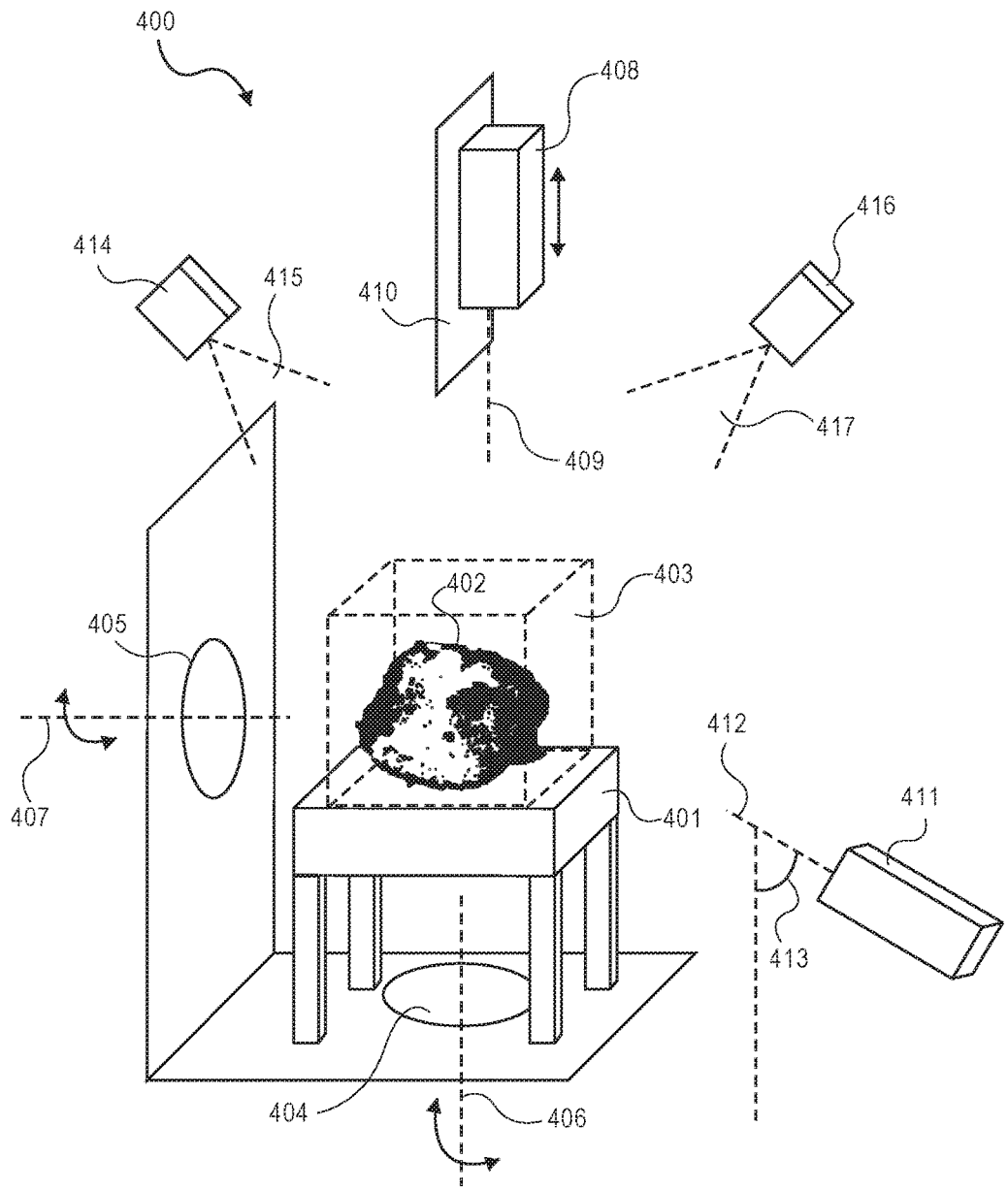
FIG. 4 is an illustration of an imaging system having a side-view camera with a "pre-tilted" position.

FIG. 4 illustrates an embodiment in which the top-down and side-view cameras are not located substantially orthogonal to one another. Shown is an imaging apparatus 400 that includes a rotatable imaging stage 401. The stage supports a biological sample 402, wherein at least a portion of the sample is within an imaging volume 403. The stage is mechanically connected to a first rotary bearing 404 and a second rotary bearing 405. The first rotary bearing has a first rotational axis 406 that is configured to project through the imaging volume, and the second rotary bearing has a second rotational axis 407 that is also configured to project through the imaging volume. The first and second rotational axes are substantially orthogonal to one another.

The imaging apparatus 400 also includes a top-down camera 408 that is configured to have a depth of focus within the imaging volume 403. The top-down camera has a top-down optical axis 409 that is substantially parallel to the first rotational axis 406 of the first rotational bearing 404. The top-down camera is mechanically connected to a translational bearing 410 configured to translate the top-down camera along a direction substantially parallel to the top-down optical axis. The imaging apparatus also includes a side-view camera 411 that is configured to have a depth of focus within the imaging volume. The side-view camera has a side-view optical axis 412 that forms an angle 413 with the first rotational axis of the first rotational bearing. The angle is within the range from 45 degrees to 135 degrees.

The imaging apparatus 400 also includes a visible light source 414. The visible light source is configured to illuminate the imaging volume 403 with visible light 415. The apparatus also includes a fluorescence excitation light source 416. The fluorescence excitation light source is configured to illuminate the imaging volume with fluorescence excitation light 417.

The angle between the side-view optical axis of the side-view camera and the first rotational axis of the rotatable imaging stage can be any value between 45 degrees and 135 degrees. For example and without limitation, the angle can be within the range from 45 degrees to 75 degrees, from 65 to 95 degrees, from 85 degrees to 115 degrees, or from 105 degrees to 135 degrees. When the angle is between 45 degrees and 90 degrees and the side-view camera is tilted upwards towards the bottom face of the biological sample, the apparatus can provide an advantage by reducing a tilt of the rotatable imaging stage. To view the bottom face of a sample with a side-view camera that is positioned substantially orthogonal to the first rotational axis, the rotatable imaging stage must significantly tilt about its second rotational axis. A challenge associated with this tilting is the force of gravity tending to pull a sample off of the tilted imaging stage. This can be a particular problem for cases in which the stage does not include clamping or other holding measures to secure the sample to the stage and prevent the sample from slipping or sliding. When the side-view camera is "pre-tilted" by a selected angle ($\theta$), in order to observe the sample at a desired view angle ($\varphi$) the imaging stage need only be tilted by a reduced angle ($\varphi-\theta$) to present the view angle to the pre-tilted side-view angle. As an illustrative and non-limiting example, when a 45-degree view angle of the bottom of a sample is desired and a substantially orthogonally positioned side-view camera is used, the rotatable imaging stage must be tilted by 45 degrees, increasing the likelihood of sample slippage. When the same 45-degree view angle is desired and a side-view camera pre-tilted by 15 degrees is used, the rotatable imaging stage must only be tilted by a reduced angle of 30 degrees, resulting in a lower likelihood of sample slippage than with the 45-degree tilted stage.

In some embodiments, the imaging apparatus also includes a preview camera. The preview camera can record reflected light imaging data of the biological sample. In some embodiments, the preview camera can record reflected light video data of the biological sample. In certain aspects, the preview camera provides real-time or substantially real-time interactive images or video of the biological sample, allowing an operator to guide the positioning of the biological sample by using continuous or nearly continuous visual feedback from the preview camera. In some embodiments, the preview camera is a camera separate from the top-down and side-view cameras. In some embodiments, the preview camera is the top-down camera. In some embodiments, the preview camera is the side-view camera. In some embodiments, the top-down camera and the side-view camera together act as the preview camera.

In some embodiments, one or both of the top-down camera and the side-view camera are capable of adaptive imaging. For example, one or both of the cameras can adapt in real-time the imaging quality and imaging function in response to motion. In some embodiments, one or both of the cameras are capable of providing a real-time preview during image-guided navigation, and also include high-sensitivity image properties when an adaptive function is turned on. Motion-sensitive feedback from, for example, the movement of the rotatable imaging stage, can be used to assess user-controlled motion commands. When motion is substantially reduced or stopped, the camera is switched to an adaptive or enhanced configuration that can include additional imaging modalities, enhanced image quality, longer integration time for a better sensitivity, overlapping of channels, noise filtering, color changes, computational results, or other alterations. In this way, the adaptive imaging configuration can allow for better detection of faint signals at the location of interest that would otherwise be difficult to appreciate with the original imaging properties in use during the real-time preview and prior to the motion-adaptive switch.

For example, one or both of the top-down camera and the side-view camera can act as a preview camera allowing an operator to interactively review a biological sample in a 3D real-time image, with an optimal fluorescence imaging sensitivity adaptively triggered in response to a change in motion. In some embodiments, the top-down camera is a preview camera having adaptive imaging capability. In some embodiments, the side-view camera is a preview camera having adaptive imaging capability. In some embodiments, both the top-down camera and the side-view camera are preview cameras having adaptive imaging capability.

The devices and methods provided herein can utilize a computing apparatus that is programmed or otherwise configured to automate and/or regulate one or more steps of the methods or features of the devices. Some embodiments provide machine executable code in a non-transitory storage medium that, when executed by a computing apparatus, implements any of the methods or operates any of the devices described herein. In some embodiments, the computing apparatus operates a power source.

In some embodiments, the apparatus comprises a computer processor that can record images of the biological sample. The recorded images can be reflected light images captured by a camera configured to detect reflected light. In some embodiments, the reflected light is visible light. The recorded images can be fluorescence images captured by an camera configured to detect fluorescent light. The computer processor can tag the recorded images with information related to the relative positions of one or more of cameras, imagers, detectors, or sensors, with respect to the rotatable imaging stage. The computer process can tag the recorded images with information related to the rotational position of the biological sample around either or both of a first and second rotational axes. The locational and positional tags can use information determined by detecting the locations and orientations of one or more marks on the rotational imaging stage.

In some embodiments, the computer processor can record, store, and/or transfer identifying information entered, for example, by an operator. The information can be used by an operator to identify, for example, a patient, source, processing facility, examination laboratory, label chemistry, or surgeon associated with a biological sample being imaged. The information can identify one or more regions of interest in a sample image. The information can be entered using keyboard input, touch input, voice input, or any other available data input processes. The touch input can be entered with a touch pen. The information can be directly linked with a particular image, video, or video frame recorded or captured by the top-down camera or the side-view camera. The information can be linked with a model constructed or rendered from recorded images as described in further detail below. The thus annotated or marked images can be sent through a wired or wireless data connection to a remote site or computer for communication and/or documentation purposes.

In some embodiments, the computer processor can control the rotation of the rotatable imaging stage. The rotation can be about one or both of the first and second rotational axes. The rotation can occur simultaneously along with image recording. The rotation can be stopped during image recording. In some embodiments, the rotation is from one predetermined position to another. In some embodiments, the rotation is to a series of multiple different predetermined positions. The computer can record images captured by one or more cameras in one or more channels or modalities at each position. As a non-limiting example, the computer can capture a reflected light image and a fluorescence image using each of the top-down and the side-view cameras at each position that the rotatable imaging stage is moved to. In some embodiments, the rotating of the imaging stage and the capturing of images can occur sequentially. In some embodiments, the rotating of the imaging stage and the capturing of images can occur simultaneously. Simultaneous stage rotation and image capturing can be particularly useful, for example, when real-time visualization of the biological sample is desired, such as during preview and positioning of the sample. The computer processor can rotate the imaging stage so that a transparent portion of the imaging stage is between the sample and one or more cameras, imagers, detectors, or sensors. Images or other information can then be recorded of the sample through the transparent portion of the imaging stage.

In some embodiments, the computer processor controls the rotation of the rotatable imaging stage entirely or in part according to movement commands entered by an operator. In some embodiments, the computer processor controls the rotation or translation of one or more light sources, cameras, mirrors, lenses, filters, or other optical components of the imaging system according to commands entered by an operator. The can be entered using keyboard input, touch input, voice input, or any other available data input processes. The touch input can be entered with a touch pen.

In some embodiments, the computer processor is connected to a touch screen by either a wired or wireless data connection. The touch screen can be used by an operator to, for example, view imaging information or enter any of the commands described above. The touch screen can be physically connected to the housing of the imaging apparatus. The touch screen can be separate from the housing of the imaging apparatus. In some embodiments, the touch screen is removably attachable to the imaging apparatus, such that it can be repeatedly docked to the imaging apparatus or removed for remote operation as needed.

Figure 5:
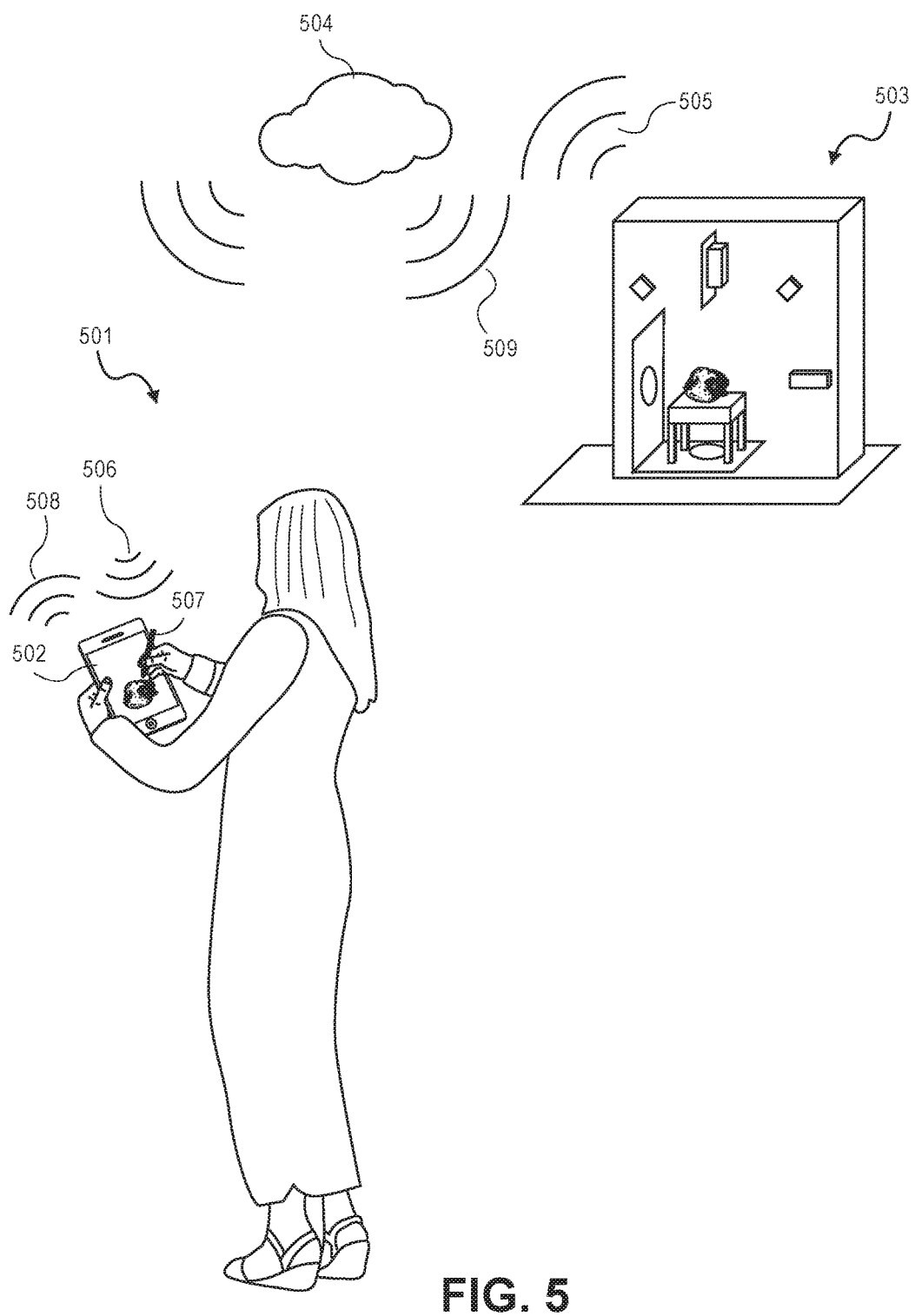
FIG. 5 is an illustration of an imaging system having a touch screen being used by an operator.

FIG. 5 illustrates the operation of a provided imaging apparatus by an operator with a touch screen. Shown in the figure is an operator 501 holding a touch screen 502. The touch screen is in wireless communication with an imaging apparatus 503. In some embodiments, and as is shown in FIG. 5, the wireless connection is via an intermediate device or system such as a cloud-based network 504, such as the internet. In some embodiments, the wireless connection is directly between the touch screen and the imaging apparatus. Visual information recorded or captured by the imaging apparatus can be transmitted 505 by the imaging apparatus and received 506 by and displayed on the touch screen. Commands or annotation can be entered by the operator using a touch pen 507 and touch screen, wherein the commands or annotation can be transmitted 508 by the touch screen and received 509 by the imaging apparatus. Information transmitted by either or both of the touch screen and the imaging apparatus can also be stored by or communicated to other devices or systems that are included in a wired or wireless network with the touch screen and/or imaging apparatus.

In some embodiments, the computer processer can construct models based on the recorded images. The models can be three-dimensional models. The models can comprise series of discrete images, each recorded as the rotatable imaging stage was at a different orientation relative to the apparatus element used in recording the images. The models can further comprise images constructed by interpolating information contained in discrete images. In some embodiments, the models are wireframe models created by translating two or more images into a polygonal mesh. The models can comprise surface information about the biological subject. The models can comprise tomographic information about the biological subject.

In some embodiments, the computer processer can render images produced from the constructed models. The rendered images can be identical to images recorded using the cameras, imagers, detectors, or sensors. The rendered images can be constructions based on information in the recorded images. The rendered images can contain images or information collected with one channel or modality. The rendered images can overlay images or information collected with two or more channels or modalities. As a non-limiting example, a rendered image can overlay reflected light information showing a visible light view of the biological sample and fluorescence information showing locations of fluorescent groups within the biological sample. Typically, when a rendered image overlays images or information from multiple channels, modalities, or models, the models are co-registered in three-dimensional space so that the image presents information for each modality as seen from a single viewpoint.

Figure 6:
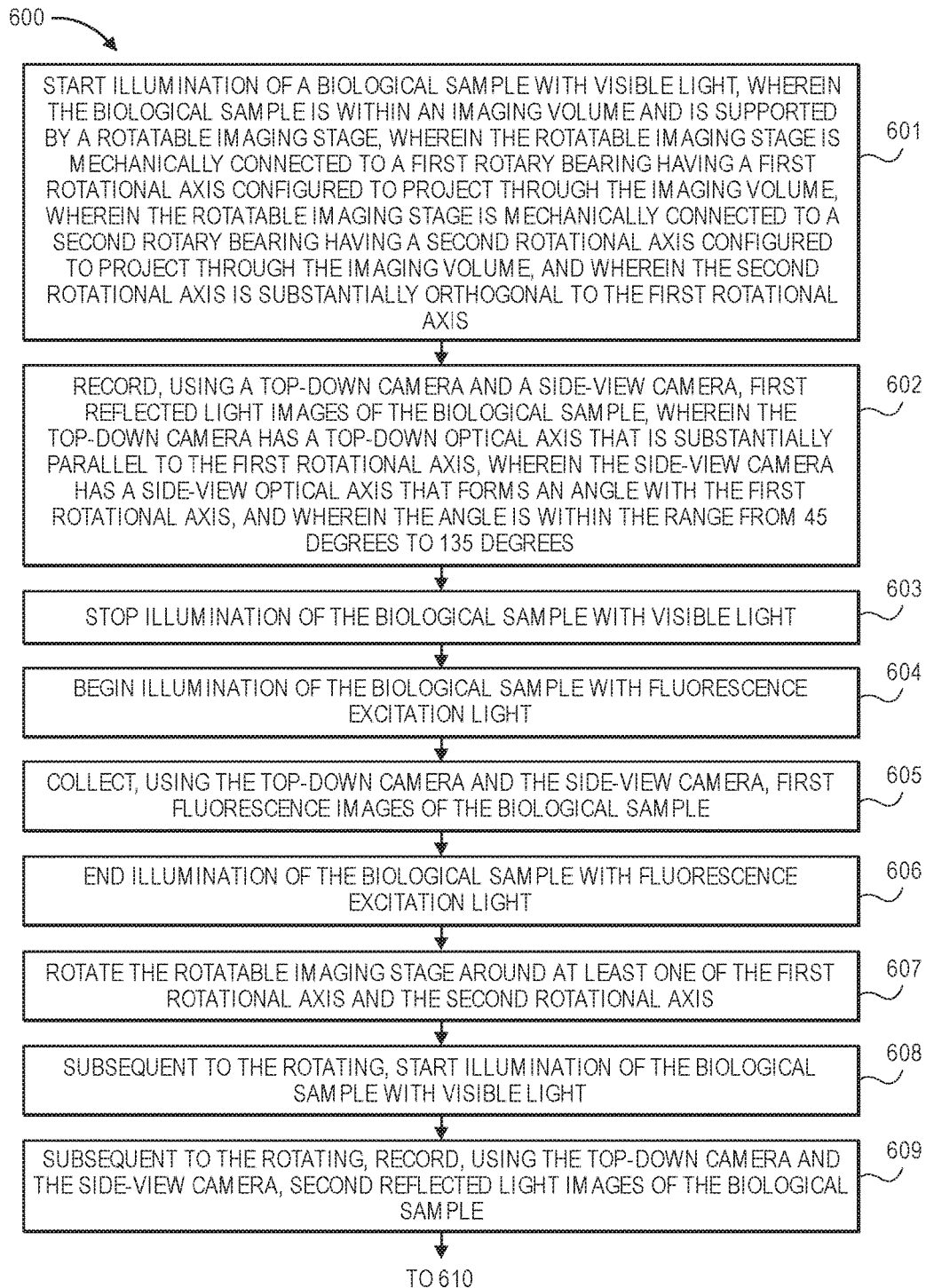
FIG. 6 is a flowchart of a process for imaging a biological sample with an imaging system having a top-down translational bearing configured to translate a top-down camera in accordance with an embodiment.
Figure 6:
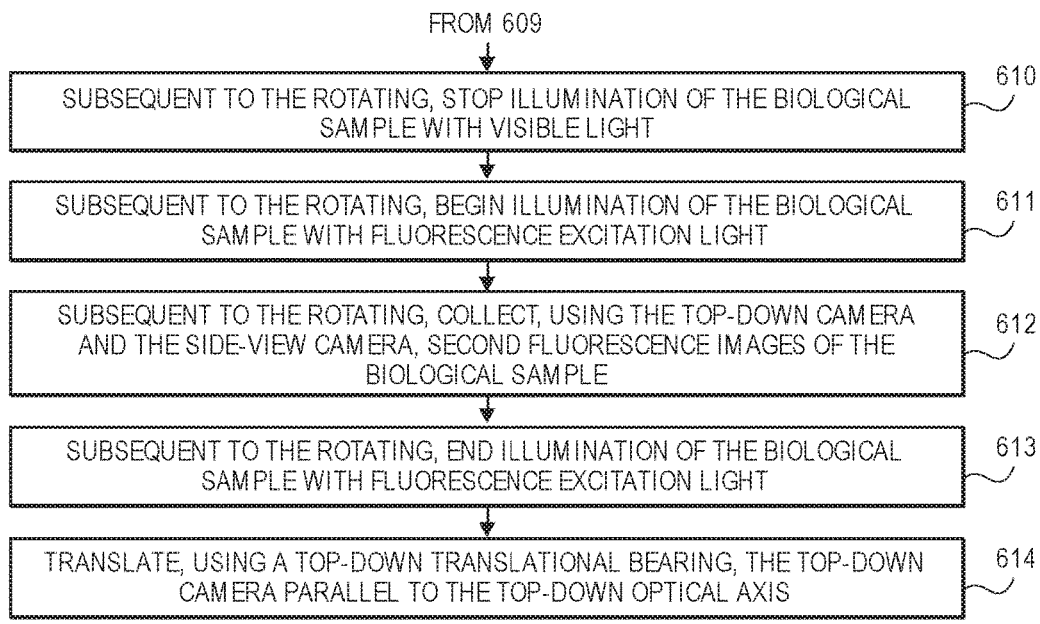

FIG. 6 presents a flowchart of a process 600 for imaging a biological sample using an imaging device having a translating top-down camera. In operation 601, illumination of a biological sample with visible light is started, wherein the biological sample is within an imaging volume and is supported by a rotatable imaging stage, wherein the rotatable imaging stage is mechanically connected to a first rotary bearing having a first rotational axis configured to project through the imaging volume, wherein the rotatable imaging stage is mechanically connected to a second rotary bearing having a second rotational axis configured to project through the imaging volume, and wherein the second rotational axis is substantially orthogonal to the first rotational axis. In operation 602, first reflected light images of the biological sample are recorded using a top-down camera and a side-view camera, wherein the top-down camera has a top-down optical axis that is substantially parallel to the first rotational axis, wherein the side-view camera has a side-view optical axis that forms an angle with the first rotational axis, and wherein the angle is within the range from 45 degrees to 135 degrees. In operation 603, illumination of the biological sample with visible light is stopped. In operation 604, illumination of the biological sample with fluorescence excitation light is begun. In operation 605, first fluorescence images of the biological sample are collected using the top-down camera and the side-view camera. In operation 606, illumination of the biological sample with fluorescent excitation light is ended. In operation 607, the rotatable imaging stage is rotated around at least one of the first rotational axis and the second rotational axis. In operation 608, illumination of the biological sample with visible light is started subsequent to the rotating. In operation 609, second reflected light images of the biological sample are recorded using the top-down camera and the side-view camera subsequent to the rotating. In operation 610, illumination of the biological sample with visible light is stopped subsequent to the rotating. In operation 611, illumination of the biological sample with fluorescence excitation light is begun subsequent to the rotating. In operation 612, second fluorescence images of the biological sample are collected using the top-down camera and the side-view camera subsequent to the rotating. In operation 613, illumination of the biological sample with fluorescence excitation light is ended subsequent to the rotating. In operation 614, the top-down camera parallel to the top-down optical axis is translated using a top-down translational bearing. The process presented in FIG. 6 can be carried out with an apparatus similar or identical to the one presented in FIG. 1.

In some embodiments, the method further comprises an operation to construct a three-dimensional reflected light model from the first and second reflected light images. In some embodiments, the method further comprises an operation to construct a three-dimensional fluorescence model from the first and second fluorescence images. In some embodiments, the method further comprises an operation to render an image produced from the reflected light model and the fluorescence model, wherein the reflected light model and the fluorescence model are co-registered in three-dimensional space. In some embodiments, the beginning of illumination of the biological sample with fluorescence excitation light includes illuminating the biological sample with two or more lasers. In some embodiments, the beginning of illumination of the biological sample with fluorescence excitation light comprises illuminating the biological sample with a filtered LED light.

Figure 7:
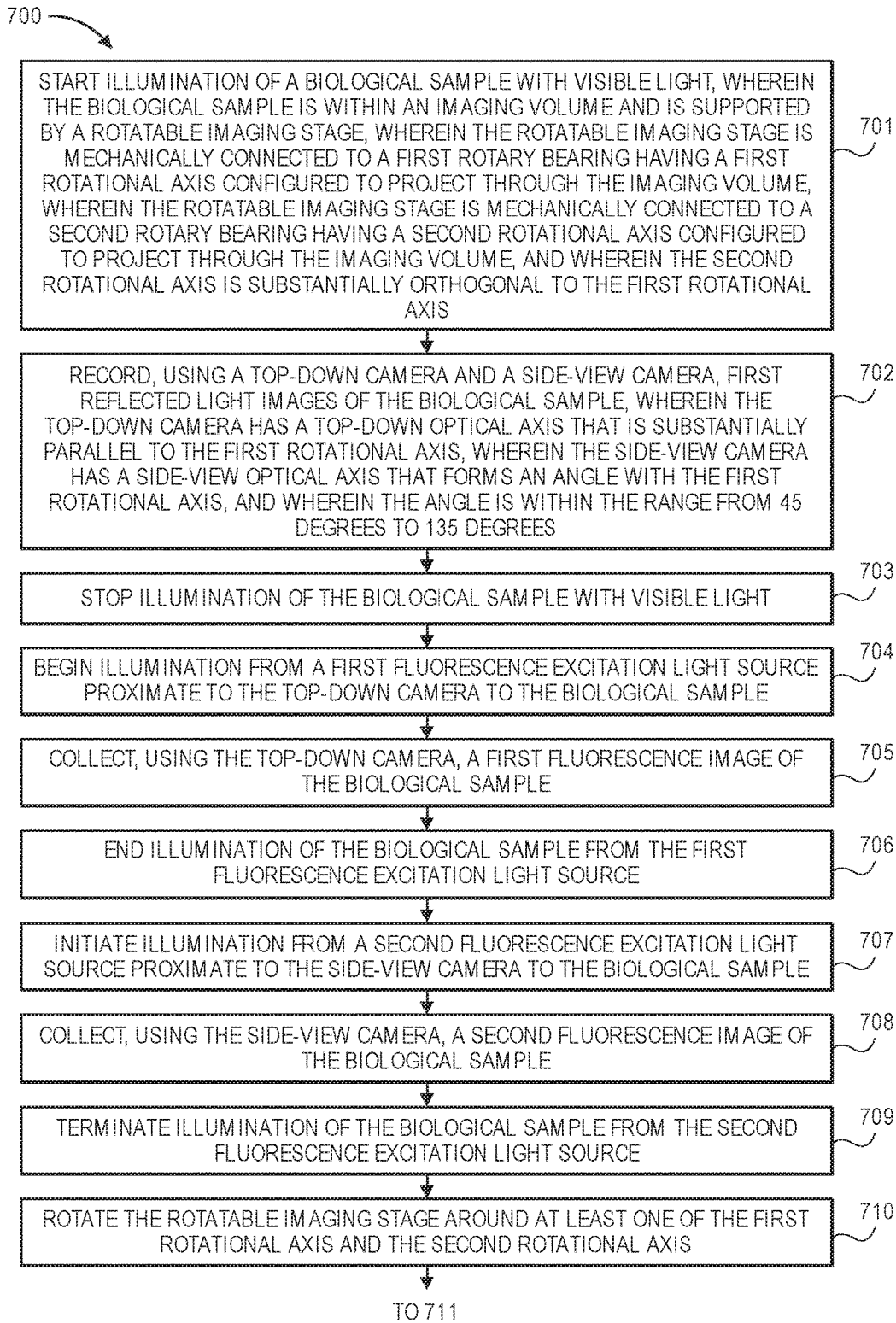
FIG. 7 is a flowchart of a process for imaging a biological sample with an imaging system having fluorescence excitation light sources configured to illuminate an imaging volume from locations proximate to top-down and side-view cameras in accordance with an embodiment.
Figure 7:
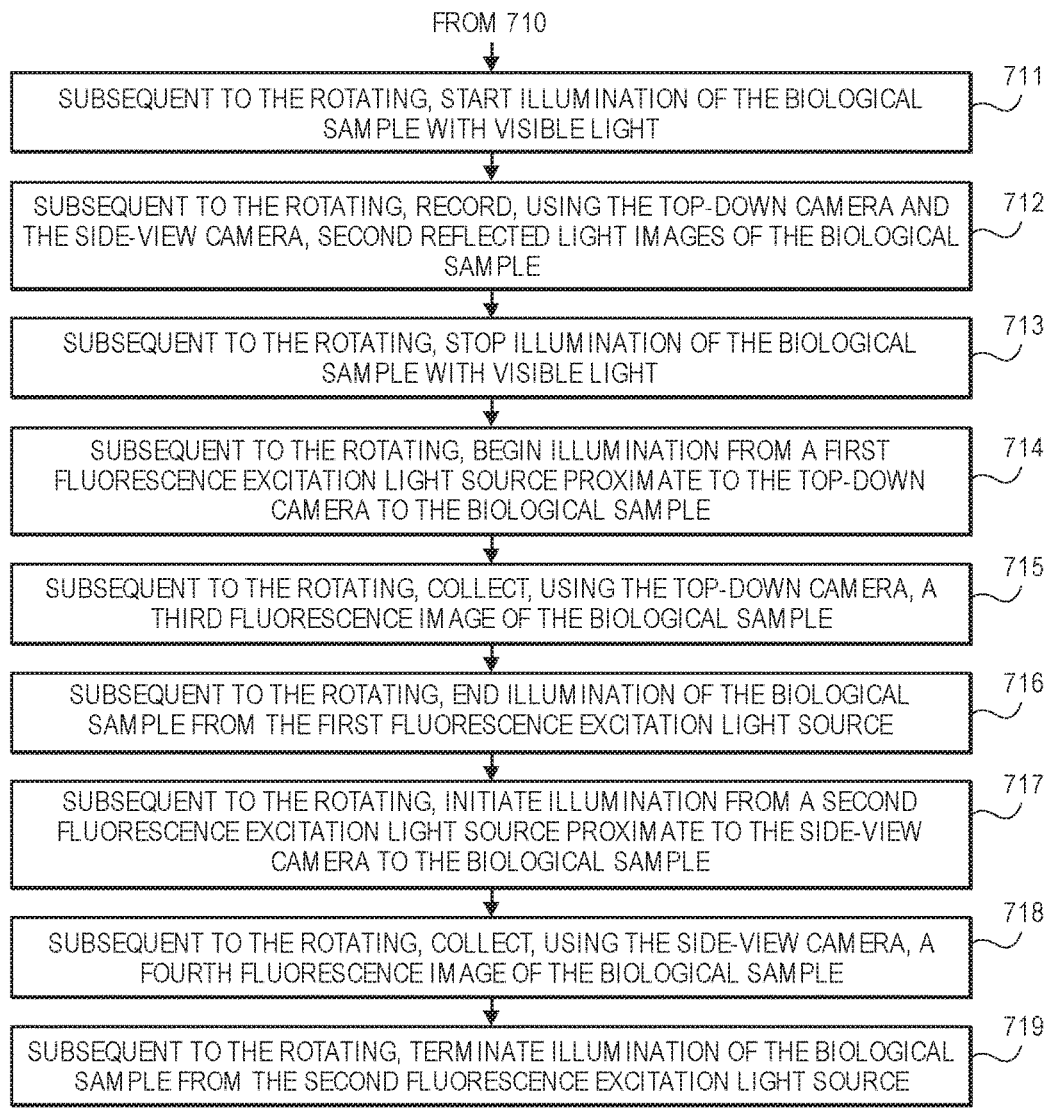

FIG. 7 presents a flowchart of a process 700 for imaging a biological sample with an imaging apparatus having first and second fluorescence excitation light sources proximate to a top-down and side-view camera, respectively. In operation 701, illumination of a biological sample with visible light is started, wherein the biological sample is within an imaging volume and is supported by a rotatable imaging stage, wherein the rotatable imaging stage is mechanically connected to a first rotary bearing having a first rotational axis configured to project through the imaging volume, wherein the rotatable imaging stage is mechanically connected to a second rotary bearing having a second rotational axis configured to project through the imaging volume, and wherein the second rotational axis is substantially orthogonal to the first rotational axis. In operation 702, first reflected light images of the biological sample are record using a top-down camera and a side-view camera, wherein the top-down camera has a top-down optical axis that is substantially parallel to the first rotational axis, wherein the side-view camera has a side-view optical axis that forms an angle with the first rotational axis, and wherein the angle is within the range from 45 degrees to 135 degrees. In operation 703, illumination of the biological sample with visible light is stopped. In operation 704, illumination from a first fluorescence excitation light source proximate to the top-down camera to the biological sample is begun. In operation 705, a first fluorescence image of the biological sample is collected using the top-down camera. In operation 706, illumination of the biological sample from the first fluorescence excitation light source is ended. In operation 707, illumination from a second fluorescence excitation light source proximate to the side-view camera to the biological sample is initiated. In operation 708, a second fluorescence image of the biological sample is collected using the side-view camera. In operation 709, illumination of the biological sample from the second fluorescence excitation light source is terminated. In operation 710, the rotatable imaging stage is rotated around at least one of the first rotational axis and the second rotational axis. In operation 711, illumination of the biological sample with visible light is started subsequent to the rotating. In operation 712, second reflected light images of the biological sample is recorded using the top-down camera and the side-view camera subsequent to the rotating. In operation 713, illumination of the biological sample with visible light is stopped subsequent to the rotating. In operation 714 illumination from a first fluorescence excitation light source proximate to the top-down camera to the biological sample is begun subsequent to the rotating. In operation 715 a third fluorescence image of the biological sample is collected using the top-down camera subsequent to the rotating. In operation 716 illumination of the biological sample from the first fluorescence excitation light source is ended subsequent to the rotating. In operation 717, illumination from a second fluorescence excitation light source proximate to the side-view camera to the biological sample is initiated subsequent to the rotating. In operation 718, a fourth fluorescence image of the biological sample is collected using the side-view camera subsequent to the rotating. In operation 719, illumination of the biological sample from the second fluorescence excitation light source is terminated subsequent to the rotating. The process presented in FIG. 7 can be carried out with an apparatus similar or identical to the one presented in FIG. 2.

In some embodiments, the operations further include constructing a three-dimensional reflected light model from the first and second reflected light images. In some embodiments, the operations further include constructing a three-dimensional fluorescence model from the first and second fluorescence images. In some embodiments, the operations further include rendering an image produced from the reflected light model and the fluorescence model, wherein the reflected light model and the fluorescence model are co-registered in three-dimensional space. In some embodiments, the beginning of illumination of the biological sample with fluorescence excitation light comprises illuminating the biological sample with two or more lasers. In some embodiments, the beginning of illumination of the biological sample with fluorescence excitation light comprises illuminating the biological sample with a filtered LED light.

Any of the above methods can be carried out with the use of a computer system that performs operations for imaging a biological sample. The operations can include starting and stopping illumination of an imaging volume by a visible light source. The operations can include beginning and ending illumination of an imaging volume by a fluorescence excitation light source. The operations can include rotating a rotatable imaging stage to two or more positions around at least one of a first rotational axis and a second rotational axis. The operations can include recording, using a top-down camera and a side-view camera, reflected light images of a biological sample. The operations can include collecting, using a top-down camera and a side-view camera, fluorescence images of a biological sample. The operations can include constructing a three-dimensional reflected light model from reflected light images recorded with a rotatable imaging stage at two or more positions. The operations can include constructing a three-dimensional fluorescence model from fluorescence images collected with a rotatable imaging stage at two or more positions. The operations can include rendering an image produced from a reflected light model and a fluorescence model, wherein the reflected light model and the fluorescence model are co-registered in three-dimensional space.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

Systems that incorporate the apparatus are also provided. Systems can include, for example, power supplies, power regulators, and other elements enabling the operation of the apparatus. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications, websites, and databases cited herein are hereby incorporated by reference in their entireties for all purposes.

What is claimed is:

1. An apparatus for imaging a biological sample, the apparatus comprising:
  a rotatable imaging stage for supporting at least a portion of a biological sample within an imaging volume, wherein the rotatable imaging stage is mechanically connected to a first rotary bearing having a first rotational axis configured to project through the imaging volume, wherein the rotatable imaging stage is mechanically connected to a second rotary bearing having a second rotational axis configured to project through the imaging volume, and wherein the second rotational axis is substantially orthogonal to the first rotational axis;
  a top-down camera configured to have a depth of focus within the imaging volume, wherein the top-down camera has a top-down optical axis that is substantially parallel to the first rotational axis;

a side-view camera configured to have a depth of focus within the imaging volume, wherein the side-view camera has a side-view optical axis that forms an angle with the first rotational axis, and wherein the angle is within the range from 45 degrees to 135 degrees;

a visible light source configured to illuminate the imaging volume;

a first fluorescence excitation light source configured to illuminate the imaging volume from a location proximate to the top-down camera; and a second fluorescence excitation light source configured to illuminate the imaging volume from a location proximate to the side-view camera.

2. The apparatus of claim 1, wherein the angle is within the range from 70 degrees to 110 degrees.

3. The apparatus of claim 1, wherein the side-view optical axis is substantially orthogonal to the first rotational axis.

4. The apparatus of claim 1, further comprising:
a computer processor operatively connected with a machine-readable non-transitory medium embodying information indicative of instructions for causing the computer processor to perform operations comprising:
starting and stopping illumination of the imaging volume by the visible light source;
beginning and ending illumination of the imaging volume by the first fluorescence excitation light source;
initiating and terminating illumination of the imaging volume by the second fluorescence excitation light source rotating the rotatable imaging stage to two or more positions around at least one of the first rotational axis and the second rotational axis;
recording, using the top-down camera and the side-view camera, reflected light images of the biological sample with the rotatable imaging stage at the two or more positions while the imaging volume is illuminated by the visible light source;
collecting, using the top-down camera, first fluorescence images of the biological sample with the rotatable imaging stage at the two or more positions while the imaging volume is illuminated by the first fluorescence excitation light source; and
collecting, using the side-view camera, second fluorescence images of the biological sample with the rotatable imaging stage at the two or more positions while the imaging volume is illuminated by the second fluorescence excitation light source.

5. The apparatus of claim 4, wherein the operations further comprise:
constructing a three-dimensional reflected light model from the reflected light images recorded with the rotatable imaging stage at the two or more positions;
constructing a three-dimensional fluorescence model from the first and the second fluorescence images collected with the rotatable imaging stage at the two or more positions; and
rendering an image produced from the reflected light model and the fluorescence model, wherein the reflected light model and the fluorescence model are co-registered in three-dimensional space.

6. The apparatus of claim 1, wherein the first and second fluorescence excitation light sources each independently comprise two or more lasers.

7. The apparatus of claim 1, wherein the first and second fluorescence excitation light sources each independently comprise a filtered LED light.

8. The apparatus of claim 1, wherein the first fluorescence excitation light source is configured to illuminate the imaging volume with a first fluorescence excitation light beam having a first fluorescence excitation light wavelength, wherein the second fluorescence excitation light source is configured to illuminate the imaging volume with a second fluorescence excitation light beam having a second fluorescence excitation light wavelength, and wherein the second fluorescence excitation wavelength is different from the first fluorescence excitation wavelength.

9. A method for imaging a biological sample, the method comprising:
starting illumination of a biological sample with visible light, wherein the biological sample is within an imaging volume and is supported by a rotatable imaging stage, wherein the rotatable imaging stage is mechanically connected to a first rotary bearing having a first rotational axis configured to project through the imaging volume, wherein the rotatable imaging stage is mechanically connected to a second rotary bearing having a second rotational axis configured to project through the imaging volume, and wherein the second rotational axis is substantially orthogonal to the first rotational axis;
recording, using a top-down camera and a side-view camera, first reflected light images of the biological sample, wherein the top-down camera has a top-down optical axis that is substantially parallel to the first rotational axis, wherein the side-view camera has a side-view optical axis that forms an angle with the first rotational axis, and wherein the angle is within the range from 45 degrees to 135 degrees;
stopping illumination of the biological sample with visible light;
beginning illumination from a first fluorescence excitation light source proximate to the top-down camera to the biological sample;
collecting, using the top-down camera, a first fluorescence image of the biological sample;
ending illumination of the biological sample from the first fluorescence excitation light source;
initiating illumination from a second fluorescence excitation light source proximate to the side-view camera to the biological sample;
collecting, using the side-view camera, a second fluorescence image of the biological sample;
terminating illumination of the biological sample from the second fluorescence excitation light source;
rotating the rotatable imaging stage around at least one of the first rotational axis and the second rotational axis;
subsequent to the rotating, starting illumination of the biological sample with visible light;
subsequent to the rotating, recording, using the top-down camera and the side-view camera, second reflected light images of the biological sample;
subsequent to the rotating, stopping illumination of the biological sample with visible light;
subsequent to the rotating, beginning illumination from a first fluorescence excitation light source proximate to the top-down camera to the biological sample;
subsequent to the rotating, collecting, using the top-down camera, a third fluorescence image of the biological sample;
subsequent to the rotating, ending illumination of the biological sample from the first fluorescence excitation light source;

subsequent to the rotating, initiating illumination from a second fluorescence excitation light source proximate to the side-view camera to the biological sample;

subsequent to the rotating, collecting, using the side-view camera, a fourth fluorescence image of the biological sample; and subsequent to the rotating, terminating illumination of the biological sample from the second fluorescence excitation light source.

10. The method of claim 9, wherein the angle is within the range from 70 degrees to 110 degrees.

11. The method of claim 9, wherein the side-view optical axis is substantially orthogonal to the first rotational axis.

12. The method of claim 9, further comprising:
constructing a three-dimensional reflected light model from the first and second reflected light images;
constructing a three-dimensional fluorescence model from the first, second, third, and fourth fluorescence images; and
rendering an image produced from the reflected light model and the fluorescence model, wherein the reflected light model and the fluorescence model are co-registered in three-dimensional space.

13. The method of claim 9, wherein the first and second fluorescence excitation light sources each independently comprise two or more lasers.

14. The method of claim 9, wherein the first and second fluorescence excitation light sources each independently comprise a filtered LED light.

15. A machine-readable non-transitory medium embodying information indicative of instructions for causing a computer processor to perform operations for imaging a biological sample, the operations comprising:
starting illumination of a biological sample with visible light, wherein the biological sample is within an imaging volume and is supported by a rotatable imaging stage, wherein the rotatable imaging stage is mechanically connected to a first rotary bearing having a first rotational axis configured to project through the imaging volume, wherein the rotatable imaging stage is mechanically connected to a second rotary bearing having a second rotational axis configured to project through the imaging volume, and wherein the second rotational axis is substantially orthogonal to the first rotational axis;
recording, using a top-down camera and a side-view camera, first reflected light images of the biological sample, wherein the top-down camera has a top-down optical axis that is substantially parallel to the first rotational axis, wherein the side-view camera has a side-view optical axis that forms an angle with the first rotational axis, and wherein the angle is within the range from 45 degrees to 135 degrees;
stopping illumination of the biological sample with visible light;
beginning illumination from a first fluorescence excitation light source proximate to the top-down camera to the biological sample;
collecting, using the top-down camera, a first fluorescence image of the biological sample;
ending illumination of the biological sample from the first fluorescence excitation light source;
initiating illumination from a second fluorescence excitation light source proximate to the side-view camera to the biological sample;
collecting, using the side-view camera, a second fluorescence image of the biological sample;
terminating illumination of the biological sample from the second fluorescence excitation light source;
rotating the rotatable imaging stage around at least one of the first rotational axis and the second rotational axis;
subsequent to the rotating, starting illumination of the biological sample with visible light;
subsequent to the rotating, recording, using the top-down camera and the side-view camera, second reflected light images of the biological sample;
subsequent to the rotating, stopping illumination of the biological sample with visible light;
subsequent to the rotating, beginning illumination from a first fluorescence excitation light source proximate to the top-down camera to the biological sample;
subsequent to the rotating, collecting, using the top-down camera, a third fluorescence image of the biological sample;
subsequent to the rotating, ending illumination of the biological sample from the first fluorescence excitation light source;
subsequent to the rotating, initiating illumination from a second fluorescence excitation light source proximate to the side-view camera to the biological sample;
subsequent to the rotating, collecting, using the side-view camera, a fourth fluorescence image of the biological sample; and
subsequent to the rotating, terminating illumination of the biological sample from the second fluorescence excitation light source.

16. The machine-readable non-transitory medium of claim 15, wherein the angle is within the range from 70 degrees to 110 degrees.

17. The machine-readable non-transitory medium of claim 15, wherein the side-view optical axis is substantially orthogonal to the first rotational axis.

18. The machine-readable non-transitory medium of claim 15, wherein the operations further comprise:
constructing a three-dimensional reflected light model from the first and second reflected light images;
constructing a three-dimensional fluorescence model from the first, second, third, and fourth fluorescence images; and
rendering an image produced from the reflected light model and the fluorescence model, wherein the reflected light model and the fluorescence model are co-registered in three-dimensional space.

19. The machine-readable non-transitory medium of claim 15, wherein the first and second fluorescence excitation light sources each independently comprise two or more lasers.

20. The machine-readable non-transitory medium of claim 15, wherein the first and second fluorescence excitation light sources each independently comprise a filtered LED light.

* * * * *